US008652366B2

(12) United States Patent
Smyth et al.

(10) Patent No.: US 8,652,366 B2
(45) Date of Patent: Feb. 18, 2014

(54) AEROSOL-MEDIATED PARTICLE SYNTHESIS

(75) Inventors: Hugh D. C. Smyth, Austin, TX (US); Ibrahim M. El-Sherbiny, El-Mansoura (EG)

(73) Assignee: Board of Regents, The University of Texas System, Austin, TX (US)

( * ) Notice: Subject to any disclaimer, the term of this patent is extended or adjusted under 35 U.S.C. 154(b) by 165 days.

(21) Appl. No.: 13/286,625

(22) Filed: Nov. 1, 2011

(65) Prior Publication Data

US 2012/0108676 A1 May 3, 2012

Related U.S. Application Data

(60) Provisional application No. 61/408,850, filed on Nov. 1, 2010.

(51) Int. Cl.
*B29B 9/00* (2006.01)

(52) U.S. Cl.
USPC .............................................. 264/5; 264/12

(58) Field of Classification Search
None
See application file for complete search history.

(56) References Cited

U.S. PATENT DOCUMENTS

| | | | | |
|---|---|---|---|---|
| 5,472,648 | A * | 12/1995 | Alisch et al. | 264/9 |
| 7,208,106 | B2 * | 4/2007 | Shekunov et al. | 264/5 |
| 7,311,861 | B2 * | 12/2007 | Lanphere et al. | 264/7 |
| 8,389,013 | B2 * | 3/2013 | Foster et al. | 424/489 |
| 2003/0109421 | A1 * | 6/2003 | Palakodaty et al. | 514/2 |
| 2004/0220081 | A1 * | 11/2004 | Kreitz et al. | 514/2 |
| 2005/0106257 | A1 * | 5/2005 | Albayrak | 424/489 |
| 2007/0154560 | A1 * | 7/2007 | Hyon | 424/489 |

OTHER PUBLICATIONS

Bailey et al., Nanoparticle formulations in pulmonary drug delivery, Med. Res. Rev., 29:196-212 (2009).
Barry et al., An in vitro analysis of the output of salbutamol from different nebulizers, European Respiratory J., 13:1164-1169 (1999).
Bauer et al., Output and Aerosol Properties of 5 Nebulizer/Compressor Systems with Arformoterol Inhalation Solution, Respiratory Care, 54(10):1342-1347 (2009).
Bergemann et al., Magnetic ion-exchange nano- and microparticles for medical, biochemical and molecular biological applications, J. Magnetism Magnetic Mater., 194:45-52 (1999).
Cao et al., Preparation of amorphous Fe2O3 powder with different particle sizes, J. Mater Chem., 7:2447-2451 (1997).
Chan et al., Synthesis and evaluation of colloidal magnetic iron oxides for the site-specific radiofrequency-induced hyperthermia of cancer, J. Magnetism Magnetic Mater., 122:374-378 (1993).
Dheu-Andries et al., Geometrical Features of Calcium-Carbohydrates Interactions, Carbohydrate Res., 124:324-332 (1983).
Dyal et al., Activity of Candida rugosa lipase immobilized on γ-Fe2O3 magnetic nanoparticles, J. Am. Chem. Soc., 125:1684-1685 (2003).

(Continued)

*Primary Examiner* — Mary F Theisen

(74) *Attorney, Agent, or Firm* — Meunier Carlin & Curfman, LLC

(57) ABSTRACT

Disclosed are aerosol-mediated methods for synthesizing particles for biomedical and drug delivery applications. The method is based on the production of particles from sprayed polymeric micro or nano-droplets obtained by, for example, an air-jet nebulization process that is followed by gelation and/or hardening in a crosslinking fluid, non-solvent, precipitating solvent, or supercritical fluid.

20 Claims, 17 Drawing Sheets

(56) References Cited

OTHER PUBLICATIONS

Grant et al., Biological interactions between polysaccharides and divalent cations: the egg-box model, FEBS Letters, 32(1):195-198 (1973).
Grinstaff et al., Magnetic properties of amorphous iron, Phys. Rev. B, 48:269-273 (1993).
Guinesi et al., The use of DSC curves to determine the acetylation degree of chitin/chitosan samples, Thermochim Acta, 444(2):128-133 (2006).
Haug et al., Uronic Acid Sequence in Alginate from Difference Sources, Carbohydrate Res., 32:217-225 (1974).
Haug et al., A Study of the Constitution of Alginic Acid by Partial Acid Hydrolysis, Acta Chem. Scand., 20:183-190 (1966).
Hess, Nebulizers: Principles and Performance, Respiratory Care, 45:609-622 (2000).
Hyeon, Chemical synthesis of magnetic nanoparticles, Chem. Commun., 8:927-934 (2003).
Jordan et al., Endocytosis of dextran and silan-coated magnetite nanoparticles and the effect of intracellular hyperthermia on human mammary carcinoma cells in vitro, J. Magnetism Magnetic Mater., 194:185-196 (1999).
Jørgensen et al., Influence of oligoguluronates on alginate gelation, kinetics, and polymer organization, Biomacromolecules 8(8):2388-2397 (2007).
Kim et al., Characterization and MRI study of surfactant-coated superparamagnetic nanoparticles administered into the rat brain, J. Magnetism Magnetic Mater., 225:256-261 (2001).
Kittur et al., Characterization of chitin, chitosan and their carboxymethyl derivatives by differential scanning calorimetry, Carbohydrate Polymers, 49:185-193 (2002).
Liu et al., Preparation and characterization of smart magnetic hydrogels and its use for drug release, J. Magnetism Magnetic Mater., 304:e397-e399 (2006).
Lübbe et al., Clinical Experiences with Magnetic Drug Targeting: A Phase I Study with 4'-Epidoxorubicin in 14 Patients with Advanced Solid Tumors, Cancer Res., 56:4686-4693 (1996).
Majeti et al., A review of chitin and chitosan applications, Reactive Functional Polymers, 46:1-27 (2000).
McGill et al., Magnetically responsive nanoparticles for drug delivery applications using low magnetic field strengths, IEEE Transaction on Nanobioscience, 8(1):33-42 (2009).
McPeck et al., Aerosol Delivery During Continuous Nebulization, Chest, 111:1200-1205 (1997).
Morales et al., In situ synthesis and magnetic studies of iron oxide nanoparticles in calcium-alginate matrix for biomedical applications, Mater. Sci. Eng. C., 28:253-257 (2008).
Morris et al., Chiroptical and stoichiometric evidence of a specific, primary dimerisation process in alginate gelation, Carbohydrate Res., 66:145-154 (1978).
Moser, Nanostructured Materials Starting Points for Advanced Materials Synthesis, Chim Ind., 80:191-197 (1998).
Ohya et al., Preparation of PEG-grafted chitosan nanoparticles as peptide drug carriers, STP Pharm. Sci., 10:77-82 (2000).
Opanasopit et al., N-Phthaloylchitosan-g-mPEG design for all-trans retinoic acid-loaded polymeric micelles, European J. Pharm. Sci., 30:424-431 (2007).
Prego et al., Chitosan-PEG nanocapsules as new carriers for oral peptide delivery Effect of chitosan pegylation degree, J. Controlled Release, 111:299-308 (2006).
Qiu et al., Environment-sensitive hydrogels for drug delivery, Adv. Drug Delivery Rev., 53(3):321-339 (2001).
Reynolds et al., Gadolinium-loaded nanoparticles: new contrast agents for magnetic resonance imaging, J. Am. Chem. Soc., 122:8940-8945 (2000).
Sanchez et al., Computer simulation of slow magnetic relaxation, J. Mag. Magn. Mater., 140-144:365-366 (1995).
Shafi et al., Sonochemical preparation of nanosized amorphous Fe-Ni alloys, J. Appl. Phys., 81:6901-6905 (1997).
Shafi et al., Sonochemical Preparation of Nanoxized Amorphous $NiFe_2O_4$ Particles, J. Phys Chem. B, 101:6409-6414 (1997).
Siegel, Gas phase synthesis and mechanical properties of nanomaterials, Analusis, 24:M10-M12 (1996).
Siegel, Proceedings of the NATO Advanced Study Institute on Mechanical Properties and Deformation Behavior of Materials Having Ultra-fine-grained Microstructures, NATO ASI Series, Series E: App. Sci., 233:509-538 (1993).
Steginsky et al., Structural determination of alginic acid and the effects of calcium binding as determined by high-field n.m.r., Carbohydrate Res., 225:11-26 (1992).
Thode et al., The influence of the Sample Preparation on Plasma Protein Adsorption Patterns on Polysaccharide-stabilized Iron Oxide Particles and N-terminal Microsequencing of Unknown Proteins, J. Drug Targeting, 5(1):35-43 (1997).
Weissleder et al., Ultrasmall superparamagnetic iron oxide: characterization of a new class of contrast agents for MR imaging, Radiology, 175:489-493 (1990).
Yao et al., A series of novel chitosan derivatives: synthesis, characterization and micellar solubilization of paclitaxel, Carbohydrate Polymers, 68:781-792 (2007).
Zhang et al., Nasal absorption enhancement of insulin using PEG-grafted chitosan nanoparticles, European J. Pharm. Biopharm., 68(3):526-34 (2008).

\* cited by examiner

AEROSOL-MEDIATED PARTICLE SYNTHESIS

CROSS REFERENCE TO RELATED APPLICATIONS

This application claims the benefit of priority to U.S. Provisional Application 61/408,850, filed on Nov. 1, 2010, which is incorporated by reference herein in its entirety.

FIELD

The subject matter disclosed herein generally relates to the field of hydrogels and to methods of preparing and using such compositions.

BACKGROUND

Over the last two decades, stimuli-responsive "smart" hydrogels, which can respond reversibly to external stimuli, such as pH, temperature and electric field, have attracted a great deal of interest due to their potential applications in various fields especially in controlled drug delivery (Qiu and Park, *Adv Drug Delivery Rev* 53(3):321-339, 2001). In the recent years, a significant body of research has focused on the development of biocompatible magnetically-responsive nanoparticles for various drug delivery and biomedical applications, such as magnetic drug targeting, enzyme immobilization, hyperthermia anti-cancer treatment, and the magnetic resonance imaging for clinical diagnosis (Morales et al., *Mater Sci Eng C* 28:253-257, 2008; Kim et al., *J Magnetism Magnetic Mater* 225:256-261, 2001; Reynolds et al., *J Am Chem Soc* 122:8940-8945, 2000; Lübbe et al., *Cancer Res* 56:4686-4693, 1996; Bergemann et al., *J Magnetism Magnetic Mater* 194:45-52, 1999; Chan et al., *J Magnetism Magnetic Mater* 122:374-378, 1993; Jordan et al., *J Magnetism Magnetic Mater* 194:185-196, 1999; Dyal et al., *J Am Chem Soc* 125:1684, 2003). The efficiency of magnetic nanoparticles in most of these applications depends particularly on the particle size distribution and the morphology of the polymer/magnetic nanoparticles (Weissleder et al., *Radiology* 175:489-493, 1990; Thode et al., *J Drug Targeting* 5:35-43, 1997).

Magnetically-responsive hydrogel nanoparticles with high saturation magnetization and high susceptibility have the ability to trigger drug release upon applying external magnetic stimuli (Liva et al., *J Magnetism Magnetic Mater* 304, 397-399, 2006). The major advantage of this drug delivery technology is attributed to the magnetic characteristics of the carrier system, which can be controlled remotely, and the biocompatibility of both the encapsulated iron oxides nanoparticles (e.g., magnetite ($Fe_3O_4$) and maghemite ($\gamma$-$Fe_2O_3$)), and the polymeric hydrogel matrices. Superparamagnetic iron oxide nanoparticles (SPIONs), which can be easily magnetized and concentrated in a specific site by applying an external magnetic field and re-dispersed again once the magnetic field is removed, have received considerable interest for drug delivery purposes (McGill et al., *IEEE Transaction on Nanobioscience* 8(1):33-42, 2009).

Production of hydrogel nanoparticles typically utilizes toxic or bio-incompatible solvents. Moreover, the processing can be costly and particle size distributions are typically very broad. Thus, there is a need for new processes that can efficiently produce nanoparticles, and even larger microparticles, with desirable particle size distributions. There is also a need for new biocompatible polymeric systems that allow the production of hydrogel particles with optimal characteristics and that use biocompatible solvents relevant to actual clinical use. The methods and compositions disclosed herein address these and other needs.

SUMMARY

In accordance with the purposes of the disclosed materials, compounds, compositions, articles, devices, and methods, as embodied and broadly described herein, the disclosed subject matter, in one aspect, relates to compounds and compositions and methods for preparing and using such compounds and compositions. In a further aspect, the disclosed subject matter relates to hydrogel micro and nanoparticles, for example, magnetically responsive particles. Methods for making the disclosed compositions using an aerosol assisted method are also disclosed. In a still further aspect, the disclosed subject matter relates to methods of using the disclosed compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
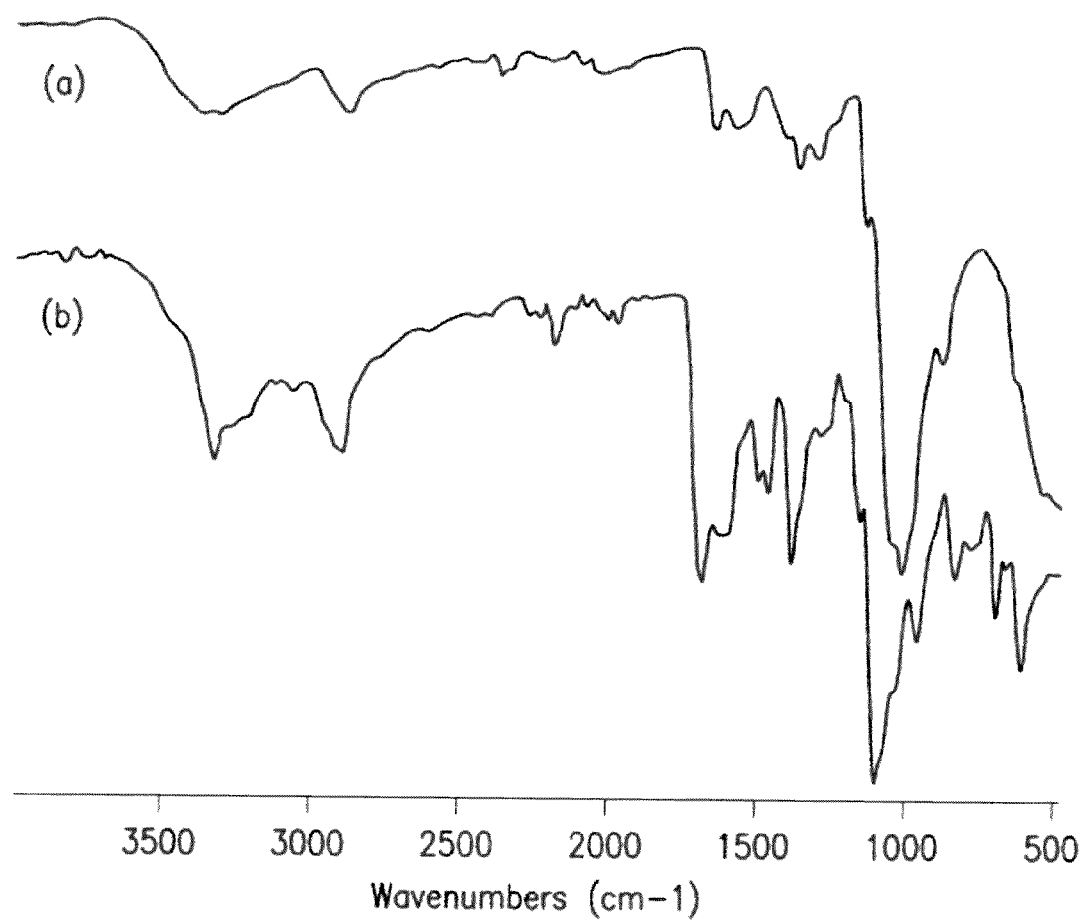
FIG. 1 contains the FTIR spectra of (a) Cs as compared to (b) the synthesized PEG-g-Cs copolymer.

The materials, compounds, compositions, articles and methods described herein may be understood more readily by reference to the following detailed description of specific aspects of the disclosed subject matter and the Examples included therein and to the Figures.

Before the present materials, compounds, compositions, articles and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such component, and the like.

"Optional" or "optionally" means that the subsequently described event or circumstance can or cannot occur, and that the description includes instances where the event or circumstance occurs and instances where it does not.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

"Treatment" or "treating" means to administer a composition to or perform a procedure on a subject with an undesired condition. The condition can include a disease. "Prevention" or "preventing" means to administer a composition to or perform a procedure on a subject at risk for the condition. The condition can include a predisposition to a disease. The effect of the administration, implantation, or performing a procedure (for treating and/or preventing) can be, but need not be limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur. It is understood that where treat or prevent are used, unless specifically indicated otherwise, the use of the other word is also expressly disclosed.

By "subject" is meant an individual. The subject can be a mammal such as a primate or a human. The term "subject" can also include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Also, disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Reference will now be made in detail to specific aspects of the disclosed materials, compounds, compositions, articles, and methods, examples of which are illustrated in the accompanying Examples and Figures.

Methods of Making

Figure 3A:
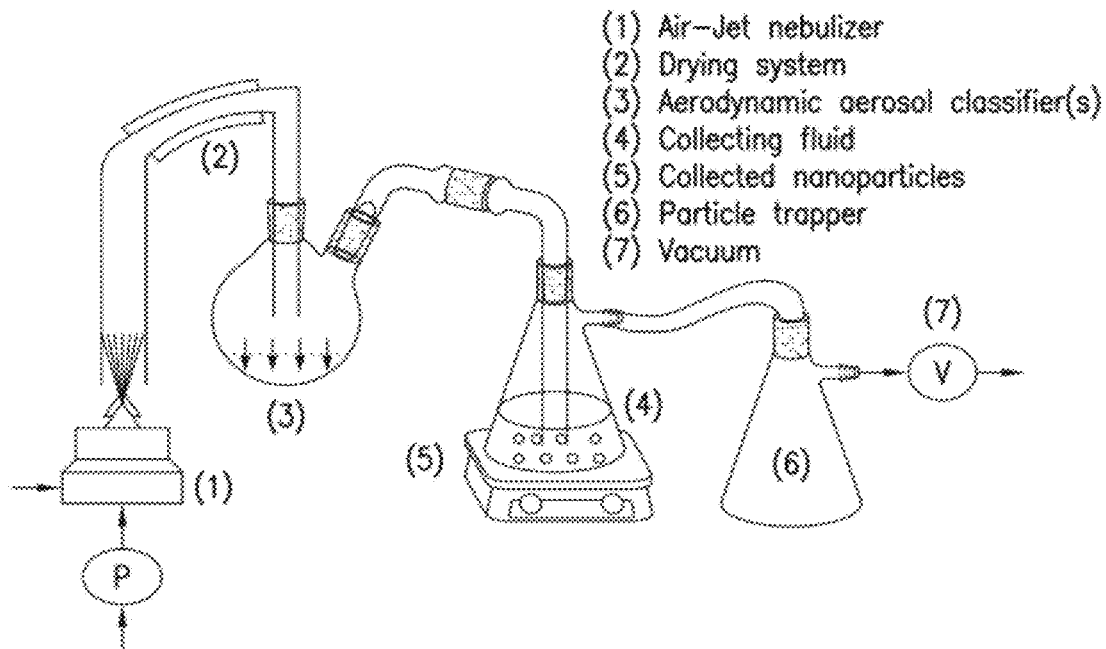
FIG. 3 is a schematic illustration of the Aerosol spray gelation-based method used in the development of the magnetic hydrogel nanoparticles. A similar apparatus can be used for magnetic hydrogel microparticles.
Figure 3B:
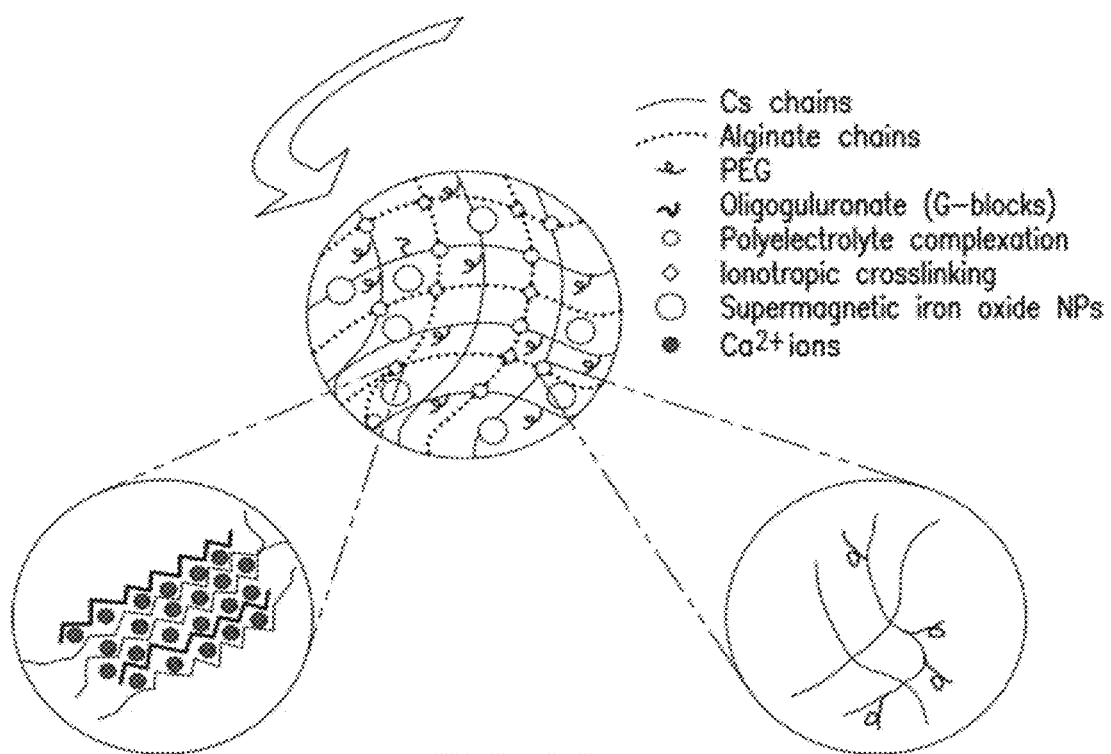
Figure 4A:
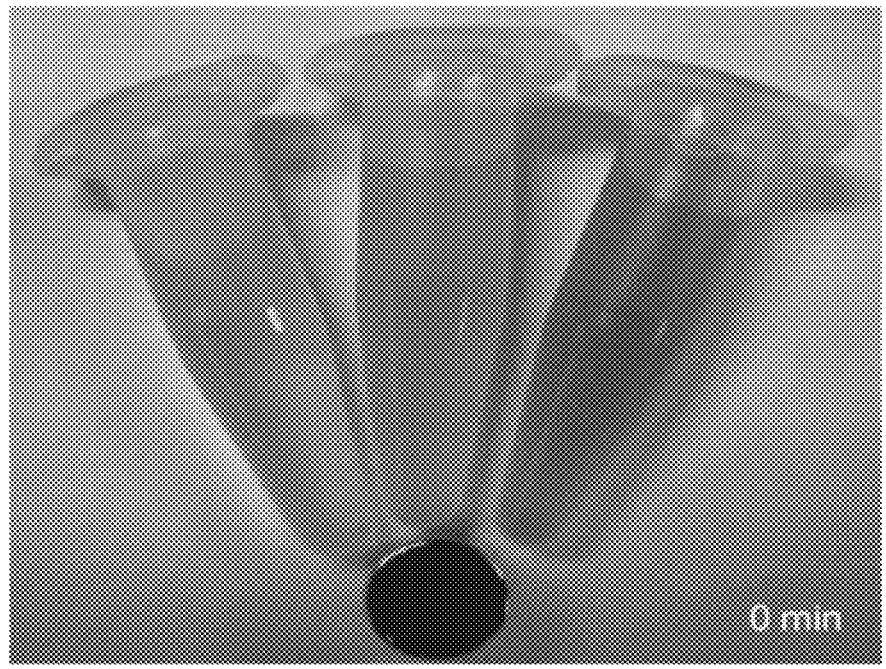
FIG. 4 is a pair of photographs showing the magnetic nature of the disclosed hydrogel nanoparticles (aqueous suspensions of different concentrations).
Figure 4B:
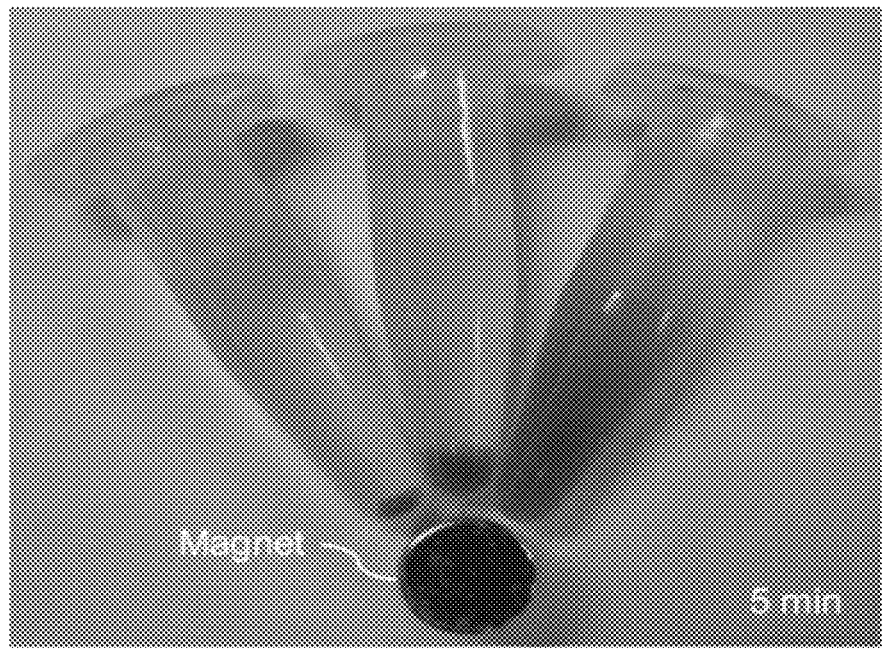
Figure 5A:
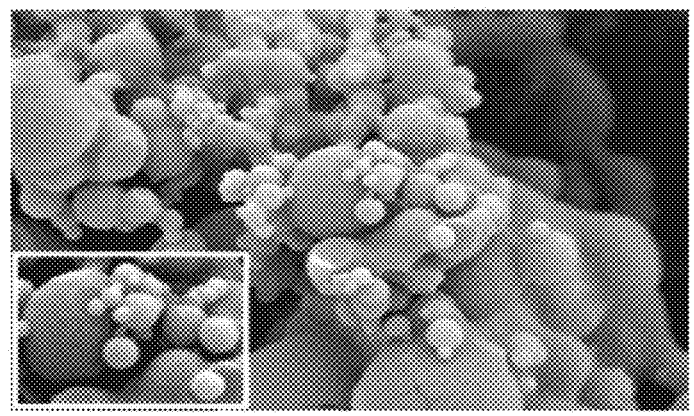
FIG. 5 is a group of scanning electron micrographs of some of the disclosed magnetic hydrogel nanoparticles; IIIA (a), and IIIB (b and c).
Figure 5B:
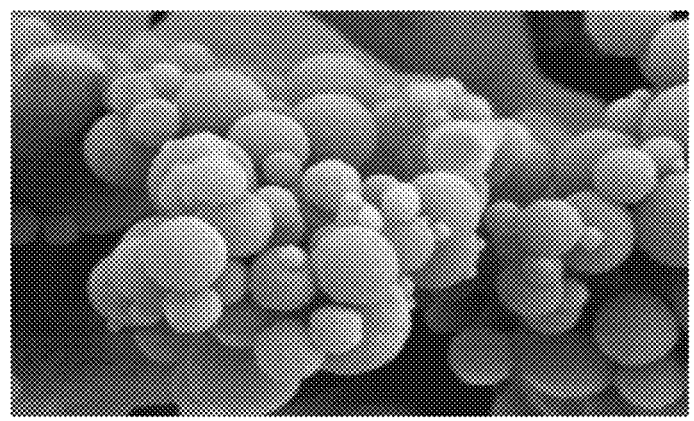
Figure 5C:
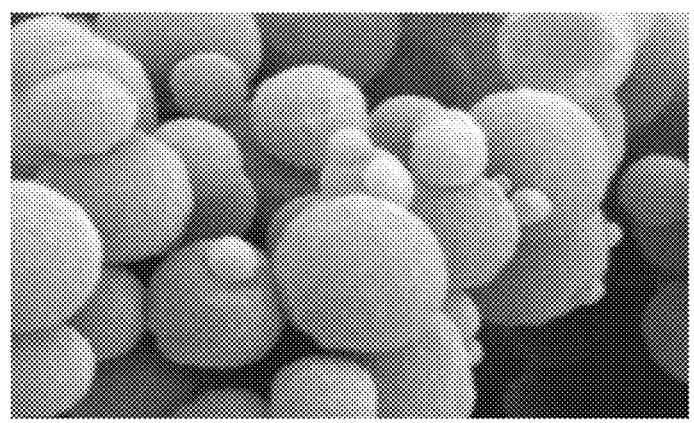

Disclosed herein are methods of preparing micro and nanoparticles for various uses. The disclosed method can generally be accomplished as roughly illustrated in FIG. 3. It is of course possible to scale up and out the lab scale process illustrated in FIG. 3 to pilot and plant scale. In the disclosed methods, a highly controllable particle synthesis can occur by aerosoliztion of materials, for example, using an air jet nebulizer or other atomizer of appropriate particle size output (1). The aerosol droplets containing material(s) dissolved or dispersed in biocompatible solvents/buffers are then conditioned (e.g., size is reduced, sizes are fractionated, and the like) (3) before bubbling through a collection fluid (4) where the aerosol droplets act as either micro/nano-reactors or micro/nano-precipitators and particles are formed (5). The particles that can be developed using this technique include, but are not limited to, polymeric nanoparticles/microparticles crosslinked through ionotropic gelation when interacting with a collecting fluid containing specific ions; polymeric nanoparticles/microparticles crosslinked through formation of polyelectrolyte complexes when interacting with other oppositely charged polymers(s) in the collection fluid; polymeric single or multiple coated drug nanoparticles; magnetic hydrogel nanoparticles (e.g., for drug delivery and biomedical applications); stable aqueous nanoparticles suspension (e.g., for paints or drug delivery applications); encapsulated hydrophobic drugs into polymeric/hydrogel nanoparticle for sustained and targeted drug release purposes; nanoparticles of hydrophobic core-hydrophilic shell or vice verse, including liposome particles.

Some advantages of the disclosed methods are that the variables and parameters of the system are easily controllable; the particle size distribution is easily controllable; biocompatible solvents can be used; it can be a continuous process; scale up to commercial scale is relatively easy; the system is relatively inexpensive; and the methods allow for a loading substance to be encapsulated, which is relevant for various industries such as drug delivery and paints.

The aerosol-mediated methods described herein can be used as alternative methods for the preparation of particles with well-defined shapes and sizes. Moreover, the obtained results indicated that the size of the particles can be optimized by changing the polymer concentration and the applied air pressure. In addition, the disclosed methods offer many advantage over other methods such relative simplicity, low cost, ease of collecting fluid and it does not involve the use of toxic solvents. All these advantages make the disclosed methods valuable for the preparation of particles for various applications particularly for drug delivery purposes.

The collection fluid that is contacted to the aerosolized mixture can be a crosslinking solution, non-solvent, precipitating solvent, or supercritical fluid, depending on the particular polymers used and the desired product characteristics. For example, when one chooses a crosslinkable polymer to aerosolize, a crosslinking solution that will crosslink the polymer would be appropriate. One example of a crosslinking fluid that can be used with certain hydrogel alginate polymers is an aqueous solution of cationic polyelectrolyte such as chitosan or a chitosan derivative, or an aqueous solution of anionic polyelectrolyte such as alginate, carrageenan, carboxymethyl cellulose, carboxymethyl chitosan, or an aqueous solution of cationic salt such as $Ca^{2+}$, $Ba^{2+}$, $Sr^{2+}$, or an aqueous solution of anionic salt such as tripolyphosphate, succinate, and citrate. Similarly, when one chooses a polymer that is to be precipitated, a non-solvent or precipitating solvent would be appropriate. Examples of the non-solvents include ethanol, aliphatic hydrocarbon, acetic acid, acetone, ethyl acetate, cyclohexanone, methanol or hexane. The precipitating solvent such as dilute hydrochloric acid, ethanol, acetone, ethyl acetate, aliphatic hydrocarbon, methanol or dilute acetic acid. For other polymers that gel, solidify or harden in supercritical fluids, then the collection fluid can be a supercritical fluid of, e.g., $CO_2$ or $H_2O$.

In a specific aspect, disclosed herein are methods of producing a particle that comprise providing an aqueous mixture of sodium alginate; aerosolizing the mixture; and contacting the aerosol with a crosslinking solution. An oligoglucoronate mixture (G-block) can be added to the aqueous mixture of alginate. The crosslinking solution can comprises a divalent cation, such as $Ca^{2+}$, $Ba^{2+}$, or $Sr^{2+}$ or a biopolymer such as chitosan or a chitosan derivative (e.g., chitosan derivatized with polyethylene glycol). In a preferred aspect, the crosslinking solution is an aqueous solution comprising chitosan derivatized with polyethylene glycol and $Ca^{2+}$ in a 1:1 ratio.

Further, the disclosed methods can involve mixing a bioactive agent and/or magnetic or magnetizable agent, as disclosed herein, into the polymer solution and aerosolizing that mixture into the collection fluid. This process allows the preparation of encapsulated bioactive, magnetic, and/or matnetizable agents in the particles. Thus, as an example, to prepared magnetic particles a magnetic or magnetizable agent can be added to an aqueous mixture of polymer (e.g., alginate). Similarly, to incorporate other agents, such as bioactive agents, they can be added to the polymer mixture before the aerosolizing step.

Particles prepared by the aerosolizing methods disclosed herein can be subject to further processing such as spray drying, compounding, blending, coating, etc.

Particles

The disclosed aerosol-mediated methods for synthesizing nano and microparticles are based on the production of particles from sprayed polymeric micro or nano-droplets obtained through an air-jet nebulization process that is followed by a gelation and/or hardening step in a crosslinking/collecting fluid. The particles disclosed herein can be synthesized to contain magnetic or magnetizable agents, rendering magnetically-responsive particles. These methods can be used for synthesizing magnetically-responsive "smart" hydrogel particles for biomedical and drug delivery applications. Similarly, the particles disclosed herein can be synthesized to contain bioactive agents, rendering drug coated or encapsulated particles for sustained and targeted drug release. Further, the particles disclosed herein can be synthesized to contain pigments or dyes, rendering stable colorant particles for paints and stains.

The methods disclosed herein can be used to prepare either or both micro and nano-particles. For example, particles in the range of from about 100 nm to 10 µm can be produced. The ability to produce a wide range of sizes is one of the advantages of the disclosed methods. In certain examples, particles from about 100 nm to about 400 nm, from about 200 to about 600 nm, from about 400 to about 800 nm from about 600 nm to about 1 µm, from about 800 nm to about 1.2 µm from about 1 to about 2 µm, from about 4 to about 6 µm, from about 5 to about 10 µm. In specific embodiments, the disclosed hydrogel particles can have a mean particle size of from about 800 nm to about 1 µm, or from about 820 nm to about 920 nm.

The particles can be made of natural or synthetic polymers. Other polymers can also be present, as the particular end use of the particle dictates. Examples of natural polymers that can be used are gelatin type A, gelatin type B, gum arabic, alginate, chitosan, carrageenan, pectin, low-methoxyl-pectin, starch, modified starch, alpha-lactalbumin, beta-lactoglobumin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, chitin, polylactides, poly-lactide-co-glycolides, derivatized chitin, polylysine, trimethyl ammonium chitosan, and carboxymethyl chitosan. Examples of synthetic polymers that can be used are polyphosphate, polystyrene, polyvinyl alcohol, polyvinyl acetate, polycarbonates, poly methyl acrylate, poly methyl methacrylate, poly ethyl acrylate, poly isopropyl acrylate, and poly vinyl pyrolidone.

In a specific embodiment, the disclosed particles can comprise alginate, such as sodium or potassium alginate. Alginate, a natural non-toxic biodegradable polyanionic copolymer, has 1,4-linked β-D-mannuronic acid (M) and α-L-guluronic acid (G) residues arranged either as consecutive blocks or in a random distribution. Sodium alginate has the ability to form hydrogels in presence of divalent cations such as $Ca^{2+}$, $Ba^{2+}$, or $Sr^{2+}$ ions (Jorgensen et al., *Biomacromolecules* 8:2388-2397, 2007) through lateral association of chain segments (ionotropic crosslinking). It has been reported that this ionotropic chelation/crosslinking occurs particularly between the cations and the G-blocks of alginate as described by the "egg-box" model (Morris et al., *Carbohydrate Res* 66:145-154, 1978; Grant et al., *FEBS Letters* 32:195, 1973) in which each divalent cation interacts with two adjacent G residues as well as with two G residues in an opposing alginate chain. Therefore, the gel strength of the alginate-based hydrogels depends mainly on the G content in addition to other parameters such as the divalent cation concentration, and the concentration and molecular weight of the alginate. Oligoguluronate residues (G-blocks) can be prepared through partial acid hydrolysis of sodium alginate. In the disclosed particles, the alginate is usually present from about 70 to about 80%, from about 80 to about 90%, or greater than about 90% by weight of the particle.

It has been found also that alginate has a strong ability to form hydrogels via polyelectrolyte complexation with cationic polymers such as chitosan (Cs) and its derivatives (Jorgensen et al., *Biomacromolecules* 8:2388-2397, 2007). Cs, a cationic polymer obtained through the alkaline N-deacetylation of chitin, has various desirable properties such as nontoxicity, biodegradability, and biocompatibility (Majeti et al., *Reactive Functional Polymers* 46:1-27, 2000). Grafting of various synthetic polymers onto the Cs backbone can further improve its characteristics and accordingly expands its applications. One of these polymers that is commonly grafted onto Cs is the poly(ethylene glycol), (PEG). PEG is a water soluble non toxic and biocompatible polymer (Ohya et al., *STP Pharm Sci* 10:77-82, 2000). Owing to the characteristics of PEG, development of polymeric micro- and nano-hydrogel particles based on PEG graft copolymerized onto Cs (PEG-g-Cs) has received some attention in drug delivery applications (Opanasopit et al., *European J Pharm Sci* 30:424-31, 2007; Prego et al., *J Controlled Release* 111:299-308, 2006; Yao et al., *Carbohydrate Polymers* 68:781-92, 2007; Zhang et al., *European J Pharm Biopharm* 68:526-34, 2008). Cs can also be derivatized with stearic acid, cholanic acid, etc.

In some specific embodiments, the disclosed particles are hydrogels comprised of either sodium alginate or a combination of sodium alginate with oligoguluronate (G-blocks) aerosolized as micro-droplets. The compositions can then be crosslinked by either ionotropic gelation in aqueous $Ca^{2+}$ solution or both ionotropic and polyelectrolyte complexation in aqueous solution of PEG-g-chitosan/$CaCl_2$.

Magnetic or Magnetizable Agents

The disclosed particles can, in certain examples, also comprise a magnetic or magnetizable agent. By "magnetizable" is meant that the composition can become magnetized (i.e., can exert a localized magnetic field) when placed in an external magnetic field. The disclosed magnetizable agents can also lose their magnetization when the external magnetic field is removed (i.e., the article exerts substantially no localized magnetic field in the absence of the applied external magnetic field).

In some specific examples, a suitable magnetic or magnetizable agent can comprise at least one paramagnetic, ferromagnetic, anti-ferromagnetic, ferrimagnetic, or superparamagnetic particle. Such particles can comprise Fe—Co, Fe—Ni, Co—Ni, and Fe—Co—Ni alloys and similar highly magnetic materials. In specific embodiments, the magnetic or magnetizable agent comprises magnetite, maghemite, or superparamagnetic iron oxide nanoparticles.

The at least one paramagnetic, ferromagnetic, anti-ferromagnetic, ferrimagnetic, or superparamagnetic particles can range in diameter from about 1 nm to about 2000 nm. Thus, a corresponding magnetic or magnetizable agent can have a diameter of from about 1 nm to about 2000 nm, from about 1 nm to about 1000 nm, from about 1 nm to about 500 nanometers, from about 500 nm to about 1000 nm, or from about 1000 to about 2000 nanometers. In other examples, the magnetic or magnetizable agent can have a diameter of less than about 2000 nm, less than about 1500 nm, less than about 1000 nm, less than about 500 nm, less than about 50 nm, less than about 25 nm, or less than about 15 nm.

Magnetic or magnetizable agents comprising at least one paramagnetic, ferromagnetic, anti-ferromagnetic, ferrimagnetic, or superparamagnetic particles can be prepared using, for example, sonochemical techniques. Sonochemical techniques can provide control over particle or crystallite size, distribution of particle sizes, and interparticle spacing. In the past few years, considerable progress has been made in the controlled synthesis of particles with sizes ranging from about 2 nm to about 50 nm.

Other techniques commonly used for synthesis of nanostructured materials include gas phase methods such as molten metal evaporation and flash vacuum thermal and laser pyrolysis decomposition of volatile organometallics (see Moser, *Chim Ind* 80:191, 1998; Sanchez et al., *J Mag Magn Mater* 365:140-144, 1995; Siegel, *Analusis* 24:M10, 1996; Siegel, *NATO ASI Series, Series E: App Sci* 233:509, 1993). Liquid phase methods use reduction of metal halides with various strong reductants, and colloidal techniques with controlled nucleation (see Moser, *Chim Ind* 80:191, 1998; Hyeon, *Chem Commun* 927-934, 2003). However, sonochemical reactions of volatile organometallics have been added to the vast range of techniques, as a general approach to the synthesis of nanophase materials.

The chemical effects of ultrasound arise from acoustic cavitation—the formation, growth, and implosive collapse of bubbles in a liquid. Violent collapse of bubbles caused by cavitation produces intense localized heating and high pressures. Sonochemical hot spots with effective local temperatures of about 5000 K, local pressures of about 1000 atmospheres, and heating and cooling rates of about $10^9$ K/s are created. The extreme conditions created inside the collapsing bubble are used for the synthesis of unusual materials from volatile organometallic compounds dissolved in the liquid. Ultrasonic reactions normally occur while maintaining a moderate argon flow to facilitate the cavitation process, insure proper mixing of reagents, and elevate the temperature of implosive bubble collapse. Vapors of volatile organometallic precursor penetrate the cavitating bubble, and decompose upon the bubble collapse; the resulting metal atoms agglomerate to form nanostructured materials.

Sonochemical synthesis with iron pentacarbonyl, $Fe(CO)_5$, cobalt tricarbonyl hydrazine, $Co(NO)(CO)_3$, and similar compounds yields nanometer-sized magnetic particles, exhibiting superparamagnetic properties (see Cao et al., *J Mater Chem* 7:2447, 1997; Grinstaff et al., *Phys Rev B* 48:269, 1993; Shafi et al., *J Appl Phys* 81:6901, 1997; Shafi et al., *J Phys Chem B,* 101:6409, 1997). Control over the nanoparticle size, as well as over the interparticle interactions, can be achieved by controlling the concentration of reagents, and by introducing surfactants, such as oleic acid, into the reaction vessel. When sonication occurs in the presence of bulky or polymeric surfactants, stable nanophased metal or metal oxide colloids are created. Surfactants can also be used to stabilize the magnetic nanoparticles in solution.

Various magnetic or magnetizable agents have been successfully synthesized, using the sonochemical method. Measurements of the magnetic properties of these nanophased materials have shown high permeability and very small hysteresis values. Preparation of magnetic or magentizable agents can be performed via a multi-step process, where synthesis of suitable precursor is followed by sonochemical synthesis and deposition of superparamagnetic particles carried out in the same reaction vessel, while delivering the volatile organometallics via the gas phase.

Thus, disclosed herein are magnetic particles, which can be prepared by the disclosed methods. The magnetic nanoparticles can, in a preferred example, be based on a combination of alginate with the G-blocks and crosslinked either with $Ca^{2+}$ (ionotropic gelation) or through polyelectrolyte complexation with the cationic PEG-g-Cs. In this particular embodiment the particles can be referred to as magnetic hydrogel particles.

Bioactive Agents

The disclosed particles can, in certain examples, also comprise a bioactive agent. Suitable bioactive agents include, but are not limited to, adrenocortical steroid; adrenocortical suppressant; aldosterone antagonist; amino acids; anabolics; anthelmintic; anti-acne agent; anti-adrenergic; anti-allergic; anti-amebic; anti-androgen; anti-anemic; anti-anginal; antiarthritic; anti-asthmatic; anti-atherosclerotic; antibacterial; anticholelithic; anticholelithogenic; anticholinergic; anticoagulant; anticoccidal; antidiabetic; antidiarrheal; antidiuretic; antidote; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimitotic; antimycotic, antineoplastic, antineutropenic, antiparasitic; antiperistaltic; antipneumocystic; antiproliferative; antiprostatic hypertrophy; antiprotozoal; antipruritic; antipsoriatic; antirheumatic; antischistosomal; antiseborrheic; antisecretory; antispasmodic; antithrombotic; antitussive; anti-ulcerative; antiurolithic; antiviral; appetite suppressant; benign prostatic hyperplasia therapy agent; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; diagnostic aid; diuretic; ectoparasiticide; enzyme inhibitor; estrogen; fibrinolytic; free oxygen radical scavenger; glucocorticoid; gonad-stimulating principle; hair growth stimulant; hemostatic; hormone; hypocholesterolemic; hypoglycemic; hypolipidemic; hypotensive; immunizing agent; immunomodulator; immunoregulator; immunostimulant; immunosuppressant; impotence therapy adjunct; inhibitor; keratolytic; LHRH agonist; liver disorder treatment, luteolysin; mucolytic; mydriatic; nasal decongestant; neuromuscular blocking agent; non-hormonal sterol derivative; oxytoxic; plasminogen activator; platelet activating factor antagonist; platelet aggregation inhibitor; potentiator; progestin; prostaglandin; prostate growth inhibitor; prothyrotropin; pulmonary surface; radioactive agent; regulator; relaxant; repartitioning agent; scabicide; sclerosing agent; selective adenosine A1 antagonist; steroid; suppressant;

symptomatic multiple sclerosis; synergist; thyroid hormone; thyroid inhibitor; thyromimetic; amyotrophic lateral sclerosis agents; unstable angina agents; uricosuric; vasoconstrictor; vasodilator; or wound healing agent. Combinations of bioactive agents can also be used. Still further, the bioactive agent can comprise an antibody, targeting agent, pigment, tag, probe, or imaging contrast agent.

Specific Embodiments

In specific examples, disclosed are magnetic hydrogel particles that comprise: polymers such as sodium alginate, wherein the particle has a mean particle size of from about 100 nm to about 10 µm, for example from about 100 nm to about 400 nm. The alginate can be from about 70 to about 80%, from about 80 to about 90%, or greater than 90% by weight of the particle. The disclosed particles can further comprise an oligoguluronate residue. The disclosed particles can further comprise a divalent cation such as $Ca^{2+}$, $Ba^{2+}$, or $Sr^{2+}$. Other polymers that can be used in the disclosed particles are chitosan or a chitosan derivative, e.g., chitosan derivatized with polyethylene glycol, stearic acid, cholanic acid, etc. A particularly preferred particle comprises chitosan derivatized with polyethylene glycol and $Ca^{2+}$. Still further examples of polymers that can be used in the disclosed particles are gelatin, gum arabic, chitosan, carrageenan, pectin, starch, hydroxypropylmethyl cellulose, carboxymethyl cellulose, or a mixture thereof. The non natural polymers include polystyrene, polyvinyl alcohol, polyvinyl acetate, polycarbonates, poly methyl acrylate, poly methyl methacrylate, poly ethyl acrylate, poly isopropyl acrylate, poly vinyl pyrolidone. In still further examples, the disclosed particles can comprise a magnetic or magnetizable agent such as magnetite, maghemite, or superparamagnetic iron oxide nanoparticles. In yet further examples, the disclosed particles can additionally contain a bioactive agent.

Method of Use

Many of the particles disclosed herein can be used to deliver bioactive agents (e.g., genes, drugs, antibodies, tags and probes, contrast and imaging agents). They can also be used as colorant particles in paints and stains, when the particles are synthesized by the disclosed methods with pigments or dyes.

One particular use involves the use of the disclosed magnetic particles to treat cystic fibrosis (CF). The disclosed magnetic particles can be loaded with a gene or drug for treating CF, and then delivered to a patient in need thereof. Then a magnetic field can be applied to thereby pull the drug or gene containing magnetic particles through the sticky secretions that are symptomatic with patients with CF. In this way, the disclosed magnetic particles can be used as a vehicle to deliver drugs and genes to their intended target. This method can also be used to deliver bioactive agents to a patient to treat tuberculosis, asthma, chronic obstructive pulmonary disease, and chronic lung infections.

In similar examples, the disclosed magnetic nanoparticles can be used to deliver active agents to an intended site in a patient. By applying a magnetic field to the patient the disclosed magnetic nanoparticles can be directed to the intended cite. Thus, drugs, gene, contrast agents for imaging, and the like can be focused magnetically at a particular site.

Administration of any of the particles disclosed herein can occur in conjunction with other therapeutic agents. Thus, the disclosed particles can be administered alone or in combination with one or more therapeutic agents. For example, a subject can be treated with a disclosed particles alone, or in combination with chemotherapeutic agents, antibodies, antibiotics, antivirals, steroidal and non-steroidal anti-inflammatories, conventional immunotherapeutic agents, cytokines, chemokines and/or growth factors. Combinations can be administered either concomitantly (e.g., as an admixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents.

The disclosed particles can be formulated in various ways, depending on the route of administration. Suitable formulations and various routes of administration are disclosed in Remington: The Science and Practice of pharmacy (19th ed.) ed. A. R. Gennaro, Mack Publishing Company, Easton, Pa. 1995.

As disclosed herein, the disclosed particles are administered to a subject in an effective amount. By "effective amount" is meant a therapeutic amount needed to achieve the desired result or results. The exact amount of the compositions required will vary from subject to subject, depending on the species, age, weight and general condition of the subject, the severity of the disorder being treated, its mode of administration and the like. Thus, it is not possible to specify an exact amount for every composition. However, an appropriate amount can be determined by one of ordinary skill in the art using only routine experimentation given the teachings herein.

The disclosed particles can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered orally, by inhalation, intramuscularly, or subcutaneously. Other compounds will be administered according to standard procedures used by those skilled in the art.

In one aspect, any of the disclosed particles can be combined with at least one pharmaceutically-acceptable carrier to produce a pharmaceutical composition. The pharmaceutical compositions can be prepared using techniques known in the art. The term "admixing" is defined as mixing the two components together so that there is no chemical reaction or physical interaction. Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Chitosan (medium MW, % N-deacetylation; 76.4%, as determined by FTIR spectroscopy and elemental analysis), monomethoxy-poly(ethylene glycol) (m-PEG, Mn 5 kDa), succinic anhydride and 1-hydroxybenzotrizole (HOBt) were supplied by Aldrich (USA). 1-Ethyl-3-(3-dimethylaminopropyl) carbodiimide hydrochloride (EDC.HCl) was obtained from Fluka Chemical Corp (Milwaukee, Wis., USA). The 4-dimethylaminopyridine (DMAP) was provided by Sigma (St. Louis, Mo., USA). Sodium alginate (low viscosity; 250 cps for a 2% solution at 25° C.), phthalic anhydride, dioxane, triethyl amine and dimethyl formamide (DMF) were obtained from Sigma-Aldrich, SIAL (St Louis, Mo., USA). The superparamagnetic iron oxide nanoparticles (SPIONs), fluidMAG-D of size 100 nm were purchased from Chemicell (Berlin, Germany). Ethanol, phosphate buffer saline (PBS pH 7.4) and all other reagents were of analytical grade and used as received.

Example 1

Preparation of Oligoguluronate (G-Blocks)

The oligoguluronate residues (G-blocks) were obtained through the partial acid hydrolysis of sodium alginate followed by fractionation of the products using a method similar to that described by Haug et al. (Haug et al., *Acta Chem Scand* 20:183-190, 1966; Haug et al., *Carbohydrate Res* 32:217-225, 1974). Specifically, sodium alginate (10 g) was dissolved in distilled water and made up to 1 L with 0.3 M HCl. The mixture was then heated at 100° C. for 6 h.

Figure 11:
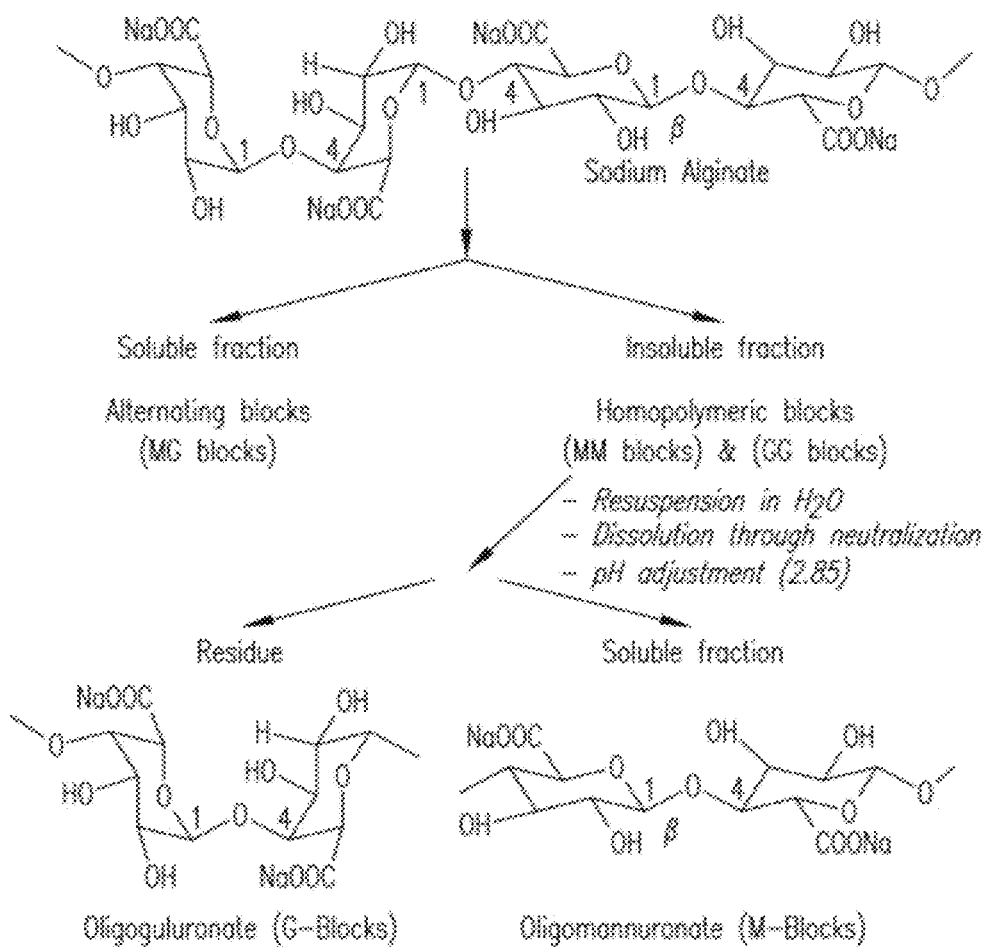
FIG. 11 is a schematic illustration of the preparation of oligoguluronate blocks (G-blocks).

The partial hydrolysis process of the alginate led to two fractions; the soluble fraction contained mainly blocks with an alternating sequence of mannuronic and guluronic acid residues (MG blocks) whereas the insoluble fraction contained homopolymeric blocks of mannuronic acid (MM blocks) and guluronic acid residues (GG blocks) as illustrated in FIG. 11. The fractionation process was achieved through collecting the oligomannuronic (MM) and oligoguluronic (GG) homopolymeric blocks, which remained intact as residues, via centrifugation for 5 min at 4000 rpm, washing, and re-suspension in distilled water. This separated mixture of homopolymeric blocks was re-suspended in water and then dissolved through neutralization by dropwise addition of dilute alkali (NaOH, 0.3 M). Afterwards, NaCl was added to make up a final concentration of 0.5% (w/v). Ethanol (2 volumes) was added and the resulting precipitate was collected by centrifugation for 5 min at 4000 rpm. The precipitate was then washed, re-dissolved in water, and the pH was adjusted to 2.85 with 1 M HCl. The oligoguluronate blocks were precipitated and collected leaving the oligomannuronate blocks in solution. The oligoguluronate fractions were desalted, and freeze-dried.

Example 2

Preparation of Cs Grafted with PEG

Figure 12:
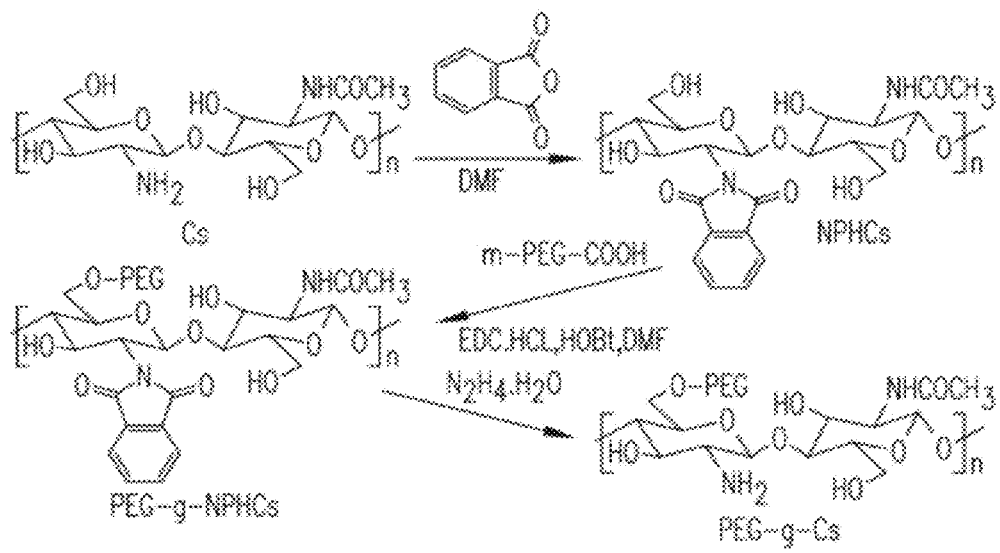
FIG. 12 is a schematic illustration of the synthesis of PEG-g-Cs copolymer.

The PEG-g-Cs copolymer was synthesized as described in El-Sherbiny et al., *J Pharm Sci* 99(5):2343-2356, 2010, and is summarized below. The overall synthesis of the PEG-g-Cs copolymer is demonstrated in FIG. 12.

(i) Preparation of N-phthaloyl Cs (NPHCs):

phthalic anhydride (44.8 g, 5 mol equivalent to pyranose rings) was reacted with 10 g of Cs in 200 ml DMF at 130° C. under dry nitrogen atmosphere for 8 h. The resulting NPHCs (pale brown solid) was then collected by filtration after precipitation in ice-water, washed with methanol and dried under vacuum at 40° C.

(ii) Preparation of m-PEG-COOH:

m-PEG (100 g, 20 mmol), DMAP (2.44 g, 20 mmol), triethylamine (2.02 g, 20 mmol) and succinic anhydride (2.4 g, 24 mmol) were dissolved in dry dioxane (350 ml) and then stirred for 2 days at room temperature under a dry nitrogen atmosphere. The dioxane was evaporated using a rotary evaporator and the residue was taken up in $CCl_4$, filtered and precipitated by diethyl ether to produce m-PEG-COOH (white powder).

(iii) Preparation of PEG-g-NPHCs:

m-PEG-COOH (37.9 g) and NPHCs (5.0 g, 0.4 mol equivalent to m-PEG-COOH) were dissolved in 75 ml of DMF. The HOBt (3.4 g, 3 mol equivalent to m-PEG-COOH) was then added, as a catalyst, with stirring at room temperature until obtaining a clear solution. Afterwards, the EDC.HCl (4.25 g, 3 mol equivalent to m-PEG-COOH) was added and the mixture was stirred overnight at room temperature. A purified PEG-g-NPHCs copolymer (5.47 g, white solid) was obtained after dialysis of the reaction mixture against distilled water and washing with ethanol.

(iv) Preparation of PEG-g-Cs:

The PEG-g-NPHCs (4.0 g) was dissolved in 15 ml of DMF and heated to 100° C. with stirring under nitrogen. Afterwards, 20 ml of hydrazine monohydrate was added and the reaction was continued for 2 h. The resulting PEG-g-Cs copolymer was purified via dialysis against a mixture of deionized ethanol and water (1:1) then dried under vacuum at 40° C.

NPHCs;

FTIR ($\upsilon_{max}$, cm$^{-1}$), 3281 (OH stretching and NH bending), 2961 (C—H stretching), 1775 and 1698 (C=O anhydride), 1395 (C=C, phthaloyl), 1058 (C—O, pyranose) and 732 (aromatic ring of phthaloyl). EA, $(C_8H_{13}NO_5)_{0.2363}$ $(C_6H_{11}NO_4)_{0.016}(C_{14}H_{13}NO_6)_{0.747}$, Anal. calculated (DS=0.98) (%): C, 55.74; H, 4.84; and N, 5.23. found (%): C, 60.31; H, 4.83; and N, 4.92.

m-PEG-COOH;

FTIR ($\upsilon_{max}$, cm$^{-1}$) 3496 (OH stretching), 2882 (C—H stretching), 1733 (C=O of carboxylic group), and 1102

(C—O—C stretching); EA, ($C_{231}H_{460}O_{117}$), Anal. calculated (%): C, 54.35 and H, 9.02. found (%): C, 56.8 and H, 9.19. PEG-g-NPHCs (5.47 g); FTIR ($\upsilon_{max}$, cm$^{-1}$) 3423 (OH stretching and NH bending), 2879 (C—H stretching), 1736 (C=O ester and anhydride), 1703 (C=O anhydride), 1096 (C—O—C stretching) and 723 (aromatic ring of phthaloyl). EA, found (%): C, 56.16; H, 4.69; and N, 5.15.

PEG-g-Cs;

FTIR ($\upsilon_{max}$, cm$^{-1}$) 3312 (OH stretching, NH bending and intermolecular H-bonding), 2879 (C—H stretching), 1708 (C=O ester) and 1096 (C—O—C stretching). EA, found (%): C, 40.46; H, 4.71; and N, 14.44.

Figure 2A:
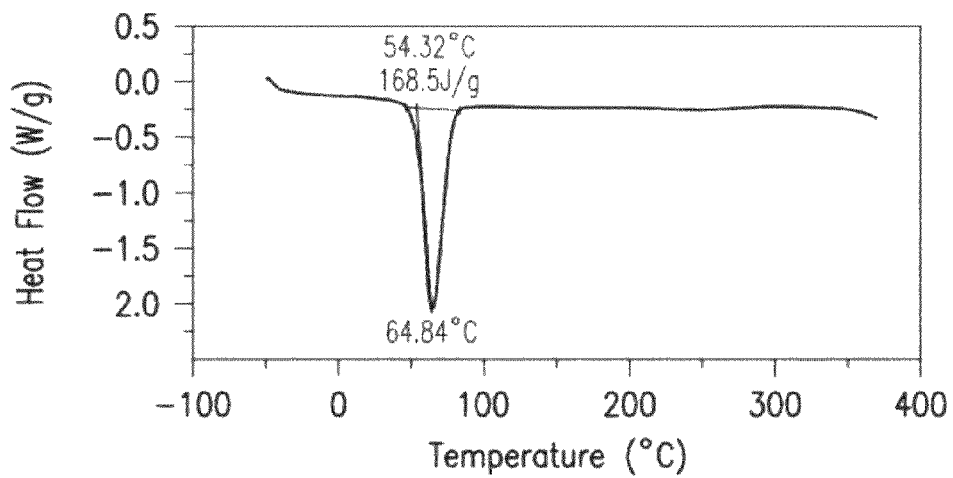
FIG. 2 is a group of DSC characterizations of the synthesized PEG-g-Cs copolymer (c) as compared to the starting materials; (a) PEG-COOH and (b) Cs.
Figure 2B:
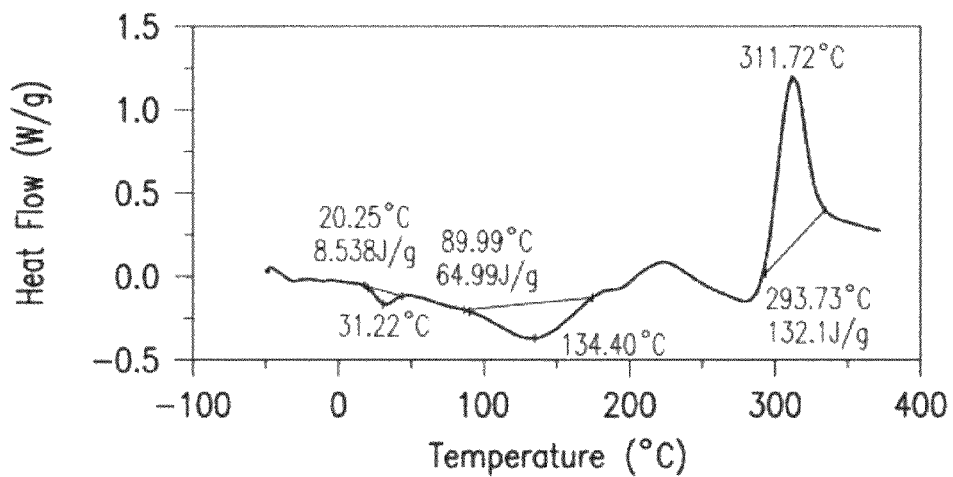
Figure 2C:
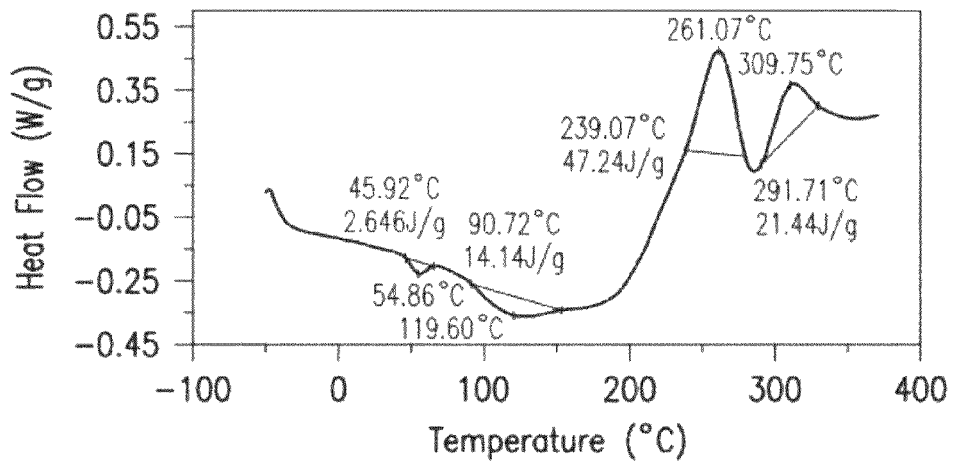

The elemental analysis was carried out using Costech ECS4010 elemental analyzer coupled to a Thermo-Finnigan Delta Plus isotope ratio mass spectrometer. The FTIR spectra was recorded using Nicolet 6700 FTIR spectrometer and the differential scanning calorimetry (DSC) was carried out using a DSC 2920 (Modulated DSC, TA Instruments) in a nitrogen atmosphere with a temperature range of −40° C. to 400° C. at a heating rate of 10° C. min$^{-1}$ for pre-weighed samples of 10-15 mg. The peaks, temperatures, and the enthalpy values were recorded.

m-PEG was modified into carboxyl-capped m-PEG precursor (m-PEG-COOH) using succinic anhydride. The free NH$_2$ groups of Cs were protected through phthaloylation process using phthalic anhydride to produce N-phthaloyl Cs (NPHCs). The preparation of NPHCs was confirmed by FTIR through appearance of peaks at 1395 and 732 cm$^{-1}$ which stand for the "aromatic C=C" and "aromatic C—H" bonds of the phthaloyl moieties, respectively. Afterwards, grafting of m-PEG-COOH onto NPHCs was carried out in DMF and the grafting % of the resulting PEG-g-NPHCs was found to be about 9.3%. The resulting PEG-g-NPHCs copolymer was also characterized by EA and FTIR. The PEG-g-Cs copolymer was then produced through the dephthaloylation of the protected NH$_2$ groups of PEG-g-NPHCs copolymer using hydrazine monohydrate. The synthesis of the PEG-g-Cs copolymer was confirmed by comparing the FTIR spectra of the copolymer with that of the starting material (Cs) as shown in FIG. 1. The synthesis of the PEG-g-Cs was also proved by studying its thermal behavior in comparison with that of starting materials, PEG-COOH and Cs as apparent in FIG. 2. For instance, the DSC thermogram of PEG-COOH (FIG. 2a) showed an endothermic band at about 65° C. which stands for its melting process. In case of the Cs thermogram (FIG. 2b), it shows an endothermic peak started at about 90° C., which can be ascribed to the loss of bound water. The Cs thermogram shows also an exotherm at 312° C. which may be attributed to the decomposition of the glucosamine units (Guinesi et al., *Thermochim Acta* 444:128-133, 2006; Kittur et al., *Carbohydrate Polymers* 49:185-193, 2002). The thermogram of PEG-g-Cs (FIG. 2c) shows an endothermic peak at 55° C., which can be attributed to the melting of the grafted PEG side chains. Also, an endotherm was observed at 119° C., which is due to the loss of bound water. The exotherms appeared at 261 and 310° C. can be ascribed to the crystallization and decomposition of the PEG-g-Cs copolymer, respectively.

Example 3

Preparation of Magnetic Hydrogel Nanoparticles Using an Aerosol-Mediated Method

Magnetic hydrogel nanoparticles were obtained using a spray method as illustrated in FIG. 3*a*. The system involves a regulated source of compressed air connected directly to an air-jet nebulizer that delivers the polymeric solutions as sprayed micro-droplets to a feed zone comprising tubing carrying droplets. This tubing was assembled to one or more of aerodynamic aerosol classifiers connected to a secondary vacuum system responsible of transporting the sprayed droplets to the crosslinker solution (collecting fluid). Then, an alternate empty glass collector was directly assembled to the primary vacuum system to recover the large hydrogel nanoparticles dragged from the secondary vacuum system.

Specifically, 2% w/v aqueous solutions of either sodium alginate or mixtures of sodium alginate with oligoguluronate of different compositions (Table 1) were prepared. Also, a 0.1% w/v aqueous solution of the synthesized copolymer, PEG-g-Cs was prepared by dissolving in 10 ml of 0.06 M acetic acid and made up to the pre-calculated volume with distilled water. Predetermined volumes of the SPIONs suspensions were added to the alginate or alginate/oligoguluronate solutions (3% SPIONs based on the total polymer weight) and homogenously distributed by sonication for 2 min. Then, the polymer/SPIONs mixtures were transferred to an Aerotech II air-jet nebulizer and aerosolized with aid of compressed air delivered at a controlled pressure of 30 psi. The generated aerosols of SPIONs/polymer micro-droplets, where directed, under vacuum, into 10 ml of a crosslinking solution of either $CaCl_2$ (0.2 M) or a (1:1) mixture of PEG-g-Cs/$CaCl_2$ under continuous mild stirring. The resulting suspensions of the swollen magnetic hydrogel nanoparticles were collected and freeze-dried. The dried hydrogel powders were then washed with distilled water to remove any residual crosslinker and then refreeze-dried. The yield (%) of the resulting dry powders of hydrogel nanoparticles was determined and the powders were stored in a desiccator at room temperature until further use.

The average size of the prepared magnetic hydrogel nanoparticles suspended in ethanol was determined by dynamic light scattering, DLS (Malvern nano-sizer, Malvern Instruments Ltd., Worcestershire, UK). The size of the particles was also estimated using microscopy techniques including light microscopy (Leica DMI6000B scope) with Leica application suite advanced fluorescence 2.2.0 build 4765 software. The average diameters (d, nm) of about 100 magnetic hydrogel nanoparticles (n=100) were recorded (see Table 1).

TABLE 1

Different compositions and particle size of the disclosed magnetic hydrogel nanoparticles

| | Polymer aq. solution (2% w/v) | | Crosslinking fluid | | Particle size, (d, nm) ± SD | | |
|---|---|---|---|---|---|---|---|
| Formulation Code | Alginate (w %) | G-block (w %) | $CaCl_2$ (0.2M) | $CaCl_2$/PEG-g-Cs (1:1) | *Dry (DLS) | #Dry (LM) | Swelled |
| IA | 100 | 00 | † | — | 936 ± 40 | 852 ± 145 | 1546 ± 84 |
| IB | 100 | 00 | — | † | 926 ± 13 | 811 ± 105 | 1498 ± 102 |

TABLE 1-continued Different compositions and particle size of the disclosed magnetic hydrogel nanoparticles

| Formulation Code | Polymer aq. solution (2% w/v) Alginate (w %) | G-block (w %) | Crosslinking fluid $CaCl_2$ (0.2M) | $CaCl_2$/PEG-g-Cs (1:1) | Particle size, (d, nm) ± SD *Dry (DLS) | #Dry (LM) | Swelled |
|---|---|---|---|---|---|---|---|
| IIA | 80 | 20 | † | — | 811 ± 162 | 770 ± 122 | 1571 ± 61 |
| IIB | 80 | 20 | — | † | 929 ± 12 | 794 ± 177 | 1427 ± 179 |
| IIIA | 70 | 30 | † | — | 941 ± 2 | 855 ± 89 | 1640 ± 75 |
| IIIB | 70 | 30 | — | † | 886 ± 2 | 800 ± 152 | 1592 ± 126 |

*Determined using DLS;
estimated using light microscopy (LM).

The prepared hydrogel nanoparticles are based on either sodium alginate or a combination of sodium alginate with oligoguluronate residue (G-blocks) aerosolized as micro-droplets followed by either ionotropic gelation in aqueous $Ca^{2+}$ solution or both ionotropic and polyelectrolyte complexation in (1:1) aqueous solution of PEG-g-Cs/$CaCl_2$ as crosslinkers as illustrated in FIG. 3*b*. In case of the ionotropic gelation of sodium alginate with $Ca^{2+}$, the carboxylate groups of subsequent guluronate (G) units in the alginate chains have suitable geometry and spacing for the binding with the $Ca^{2+}$ ions (Dheu-Andries et al., *Carbohydrate Res* 124:324-332, 1983) in addition to the higher affinity of the G units towards binding with the $Ca^{2+}$ than their mannuronate (M) counterparts (Steginsky et al., *Carbohydrate Res* 225:11-26, 1992). This type of binding has been described by the "egg-box" model (Morris et al., *Carbohydrate Res* 66:145-154, 1978; Grant et al., *FEBS Letters* 32:195, 1973). Therefore, the gel strength of alginate-based hydrogels depends mainly on the G content of the alginate in addition to the other factors such as, the calcium ion concentration, and the molecular weight and concentration of the alginate. In a recent study (Jorgensen et al., *Biomacromolecules* 8:2388-2397, 2007), free G-blocks were added to alginate solutions and the effects of this addition onto the gel strength, gelling kinetics, and syneresis of the formed alginate-based hydrogels were investigated. The results of the study showed that the free G-blocks are involved in the $Ca^{2+}$-mediated bonds formed between guluronic acid sequences within the polymeric alginates (FIG. 3*b*) (Jorgensen et al., *Biomacromolecules* 8:2388-2397, 2007). In other words, the added oligoguluronate (G-blocks) competes with the alginate chains for the $Ca^{2+}$ ions. However, the study indicated that presence of free G-blocks led to an increase in the gelation time. Also, the gel strength of the formed alginate hydrogels found to decrease with increasing amount of the free G-blocks. This reduction in the gel strength can be attributed to the lower molecular weight and viscosity of the added oligoguluronate (G-blocks) as compared to the polymeric alginate.

The disclosed hydrogel nanoparticles showed a considerable magnetically-responsive nature as apparent in FIG. 4. The figure reveals the relatively fast response of the hydrogel nanoparticles in their aqueous suspension to an external magnetic field.

As shown in Table 1, the size of the disclosed magnetic hydrogel nanoparticles was found to be in the range of 811±162 to 941±2 nm as determined by dynamic light scattering (DLS). From the table, it seems, in most formulations, that crosslinking of the hydrogel nanoparticles with a mixture of $Ca^{2+}$/PEG-g-Cs (1:1) relatively reduces the particle size as compared to the particles crosslinked with only one crosslinking agent ($Ca^{2+}$). For instance, the particles IIIA (crosslinked with $Ca^{2+}$ only) showed an average size of 941±2 nm. This size was reduced to 886±2 nm in case of the particles IIIB (crosslinked with $Ca^{2+}$/PEG-g-Cs). This effect of the crosslinking agents onto the size of the disclosed hydrogel nanoparticles was found statistically significant ($p=0.0415$). However, these differences in particle size do not appear to be practically significant. Also, it was noted from the size data that, in general, increasing the percentage of alginate in the magnetic hydrogel nanoparticles has a non significant effect on the particle size ($p=0.7702$). This can be attributed to the fact that not only sodium alginate but also the oligoguluronate (G-blocks) is participating in the crosslinking process either ionotropically with the $Ca^{2+}$ ions or through polyelectrolyte complexation with the cationic PEG-g-Cs copolymer (Jorgensen et al., *Biomacromolecules* 8:2388-2397, 2007). These effects of both the type of crosslinking agent and alginate % on the particle size were also confirmed through the particles size determination using light microscopy as shown in Table 1.

Example 4

Surface Morphology

The morphology of the disclosed magnetic hydrogel nanoparticles was investigated by SEM (Zeiss supra 40 VP scanning electron microscope). Dry magnetic nanoparticles were mounted on aluminum stubs with double-sided conducting carbon tapes and coated with a 50/50 mixture of Pt/Pd to minimize surface charging. The samples were scanned at an accelerating voltage of 10 KV.

FIG. 5 shows the scanning electron micrographs of some of the disclosed magnetic hydrogel nanoparticles. From the figure, the hydrogel nanoparticles have, in general, spherical shapes with relatively smooth surfaces. However, the extent of surface regularity and smoothness seems to vary upon changing the type of the used crosslinking agent. For instance, the hydrogel nanoparticles developed using only $Ca^{2+}$ as a crosslinking agent (FIG. 5*a*) showed a spherical morphology with highly smooth, dense and integrated surfaces. However, nanoparticles showed a relatively rough surface when crosslinked with a mixture of $Ca^{2+}$ and PEG-g-Cs (FIG. 5*b*). This surface morphology of the nanoparticles crosslinked with both $Ca^{2+}$ and PEG-g-Cs can be seen more clearly in FIG. 5*c*.

Example 5

Transmission Electron Microscopy

A Jeol 2010F field emission transmission electron microscope (TEM) was used to obtain transmission electron micrographs of the disclosed magnetic hydrogel nanoparticles at accelerating voltage of 200 kV. Also, the iron and calcium contents of the particles were estimated using energy-dispersive X-ray spectroscopy, EDS (Oxford INCA) attached to the TEM with aid of Silicon detector at an accelerating voltage of 20 kV and a magnification of 120,000×.

Figure 6A:
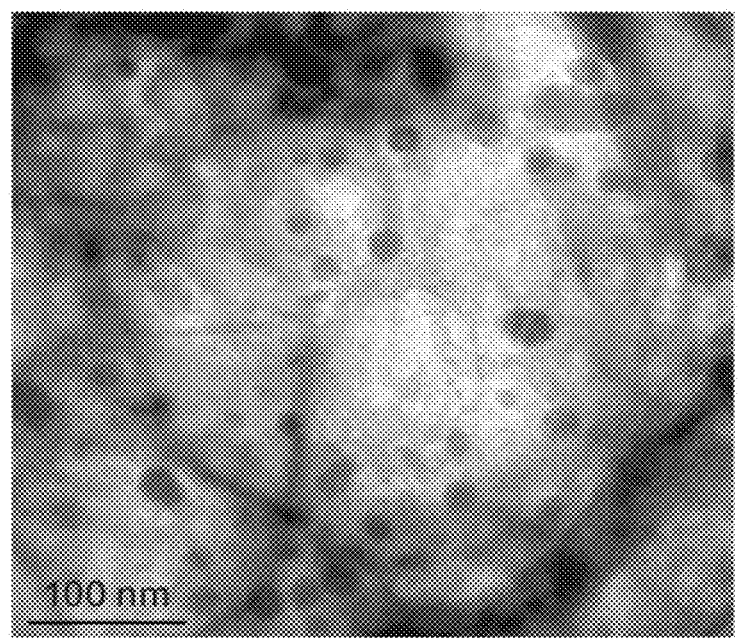
FIG. 6 contains (a) transmission electron micrographs (TEM) of the disclosed magnetic hydrogel nanoparticles, and (b) the iron and calcium contents of the magnetic hydrogels as determined by the EDS.
Figure 6B:
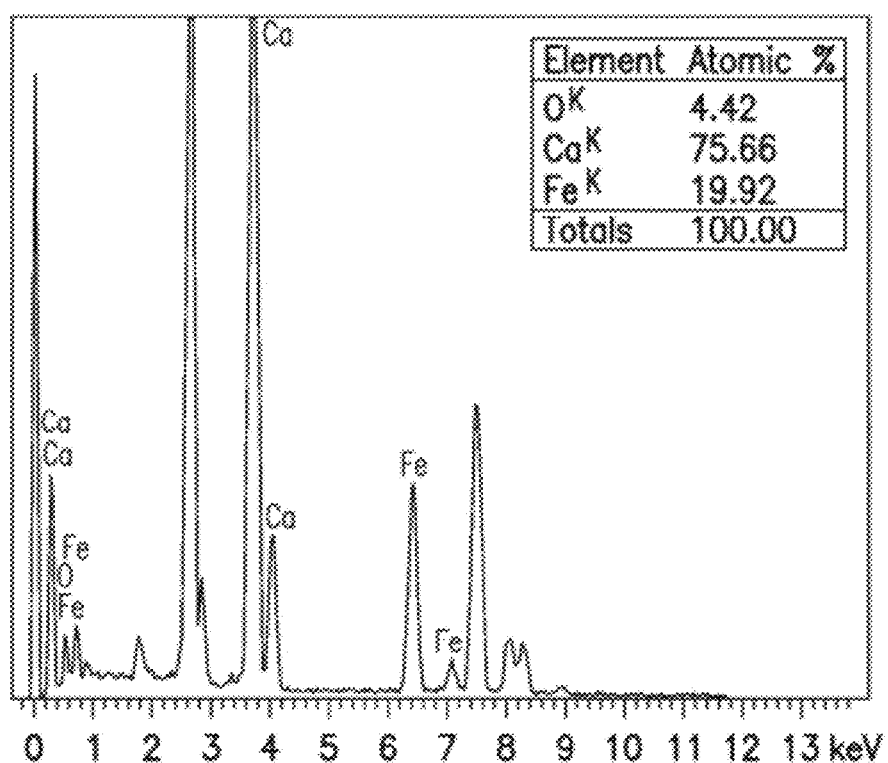

FIG. 6a shows the transmission electron microscopy (TEM) images of the disclosed magnetic hydrogel nanoparticles. The figure reveals a relatively homogenous distribution of the magnetic cores (SPIONs) nanoparticles throughout the matrix of the hydrogel particles. The content of the iron cores (atomic %) within the hydrogel nanoparticles was also estimated with the aid of energy-dispersive X-ray spectroscopy, EDS as illustrated in FIG. 6b. From the figure, the atomic iron content (%) was found to be about 20%.

Example 6

Dynamic Swelling Study

The swelling characteristics of the disclosed magnetic hydrogel nanoparticles in PBS (pH 7.4) was investigated by determining the increase in the particle diameter (d, nm) at different time intervals; 2, 5 and 10 min using light microscopy (Leica DMI6000B scope) with Leica application suite advanced fluorescence 2.2.0 build 4765 software.

Figure 7:
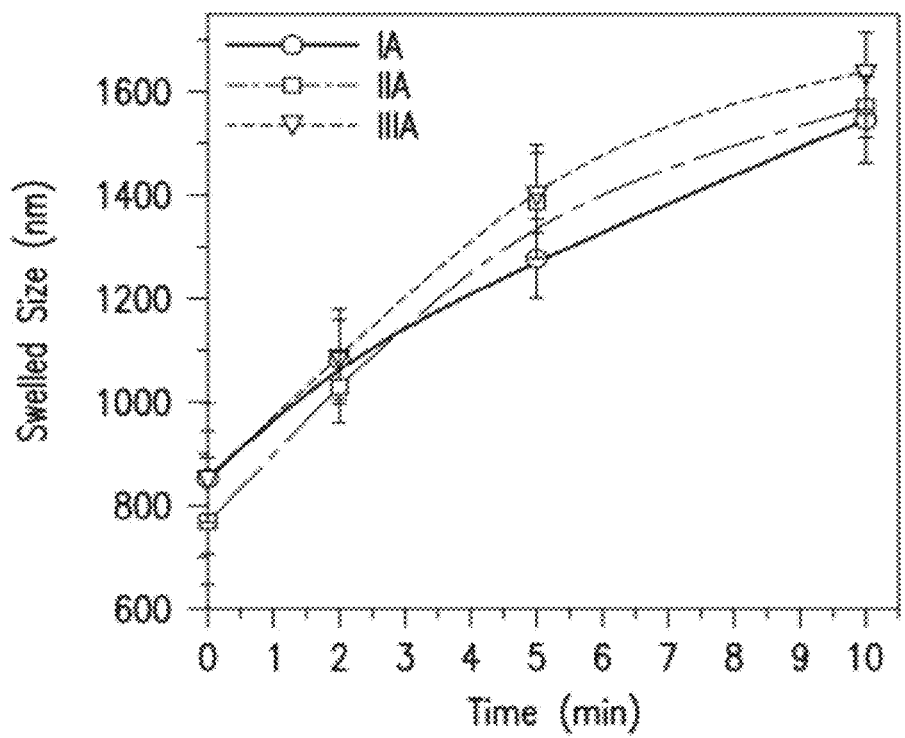
FIG. 7 is a graph showing dynamic swelling of the magnetic hydrogel nanoparticles crosslinked with $CaCl_2$ in PBS, pH 7.4.
Figure 8:
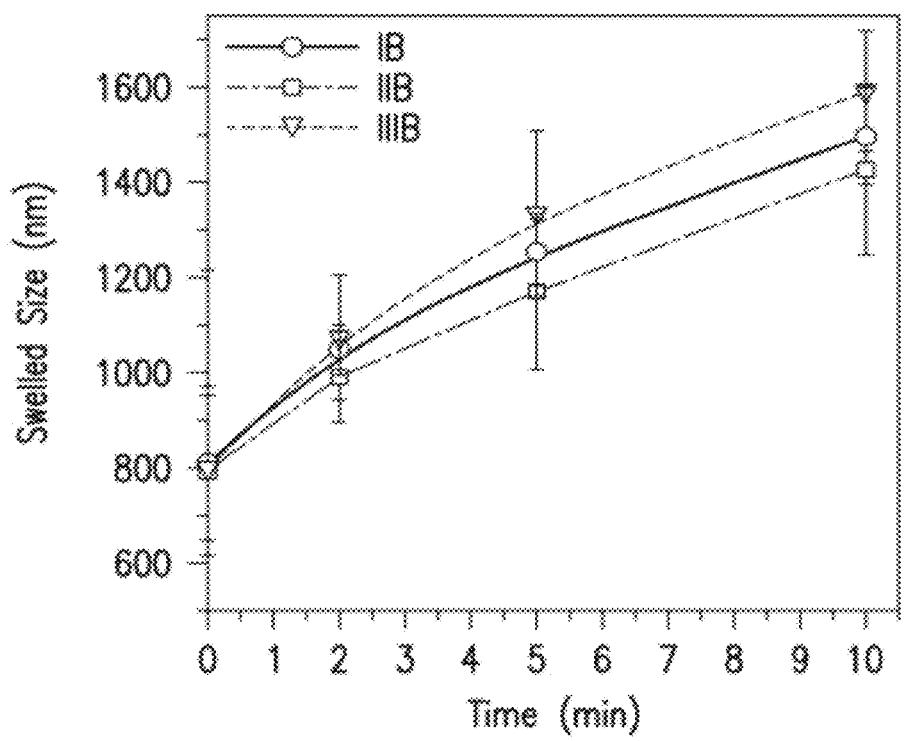
FIG. 8 is a graph showing dynamic swelling of the magnetic hydrogel nanoparticles crosslinked with $CaCl_2$/PEG-g-Cs (1:1) in PBS, pH 7.4.
Figure 9A:
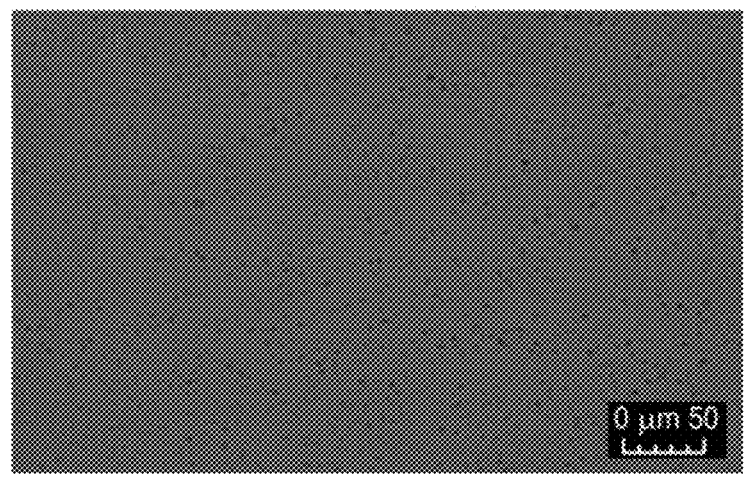
FIG. 9 is a group of microscopic images illustrating the differences in size of some of the disclosed magnetic hydrogel nanoparticles (a) dry IIIB NPs, (b) dry IIIA NPs, and (c) swelled IIIA NPs in PBS, pH 7.4.
Figure 9B:
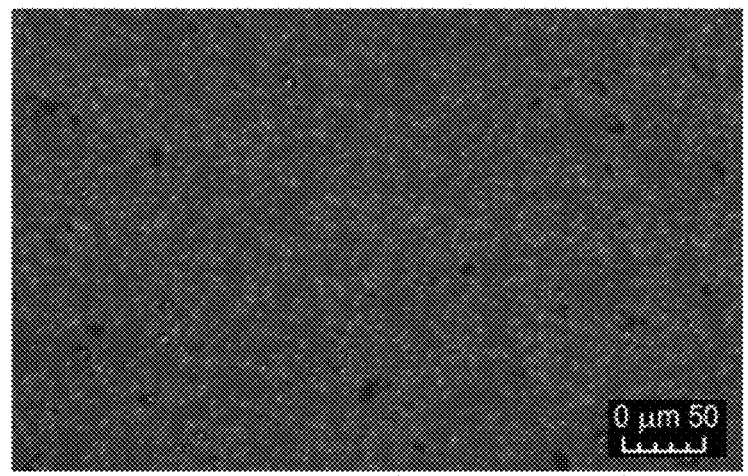
Figure 9C:
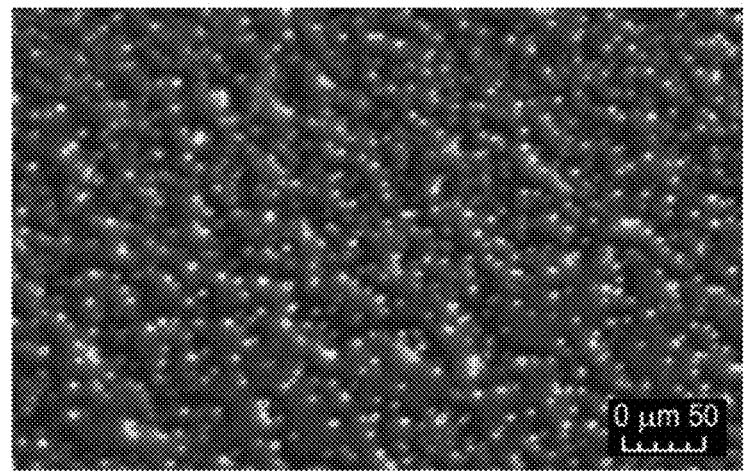

The swelling patterns of the prepared magnetic hydrogel nanoparticles in PBS, pH 7.4 are illustrated in FIGS. 7 and 8. The swelling data was obtained by measuring the increase in the diameters (d, nm) of the hydrogel nanoparticles with time using light microscopy. From the swelling data, it seems that, the hydrogel nanoparticles prepared using a mixture of $Ca^{2+}$ and PEG-g-Cs as a crosslinking agent attained relatively lower swelling values than the corresponding formulations that crosslinked only with $Ca^{2+}$. For instance, after 10 min of swelling, the hydrogel nanoparticles, IIIB (crosslinked with both $Ca^{2+}$ and PEG-g-Cs) attained a swelled size of 1592±126 nm as compared to the nanoparticles, IIIA (crosslinked with $Ca^{2+}$), which attained a swelled size of 1639±75 nm. This behavior can be attributed to increasing the crosslinking extent of the particles upon using two types of crosslinkings (ionotropic and polyelectrolyte complexation) than using only ionotropic crosslinking with $Ca^{2+}$. This effect of the crosslinker type onto the swelling values attained at equilibrium was found to be statistically significant (p=0.0001). Moreover, from the swelling patterns shown in both FIGS. 7 and 8; although, both alginate and oligoguluronate (G-blocks) contribute in the crosslinking process, it seems, in general, that increasing the alginate percentage in the disclosed nanoparticles tends to increase the crosslinking extent and consequently reduces the swelled sizes. This confirms the higher ability of the alginate as compared to the G-blocks to interact with the crosslinking agents which is in agreement with the literature (Jorgensen et al., *Biomacromolecules* 8:2388-2397, 2007). FIG. 9 shows some microscopic images that illustrate the differences in size of some of the disclosed magnetic hydrogel nanoparticles before and after attaining the equilibrium swelling.

Example 7

Statistical Analysis and Optimization of the Magnetic Hydrogel Nanoparticles by a $2^k$ Factorial Design The obtained results were analyzed and expressed as mean±SD. A 2k factorial design was used to estimate the effect of the different formulation's parameters such as the alginate % and the type of crosslinking agent onto the characteristics of the disclosed magnetic hydrogel nanoparticles such as particle size and equilibrium swelling for further optimizations. Also, the statistical significance was analyzed using ANOVA (Statgraphics Plus version 5.0 software). Differences were considered significant at the level of p<0.05.

A discontinuous $2^k$ factorial design was performed to investigate the effect of the alginate % and type of crosslinking agent and their interaction onto the characteristics of prepared magnetic hydrogel nanoparticles. The analysis was performed using Pareto charts, response surface methodology, and the contour of estimated response surface for three levels of variations in the alginate (%) factor (70, 80 and 100%, coded as −1, 0 and +1, respectively) plus two levels of variations in the second factor; the crosslinker type ($Ca^{2+}$ and $Ca^{2+}$/copolymer; coded as −1, and +1, respectively). Both the particle size and equilibrium swelling values were used as response variables. The analysis of variance for both particle size and equilibrium swelling was performed by Statgraphics 5.0 and the most influential factors were estimated at 95% confidence level.

Figures 1, 10:
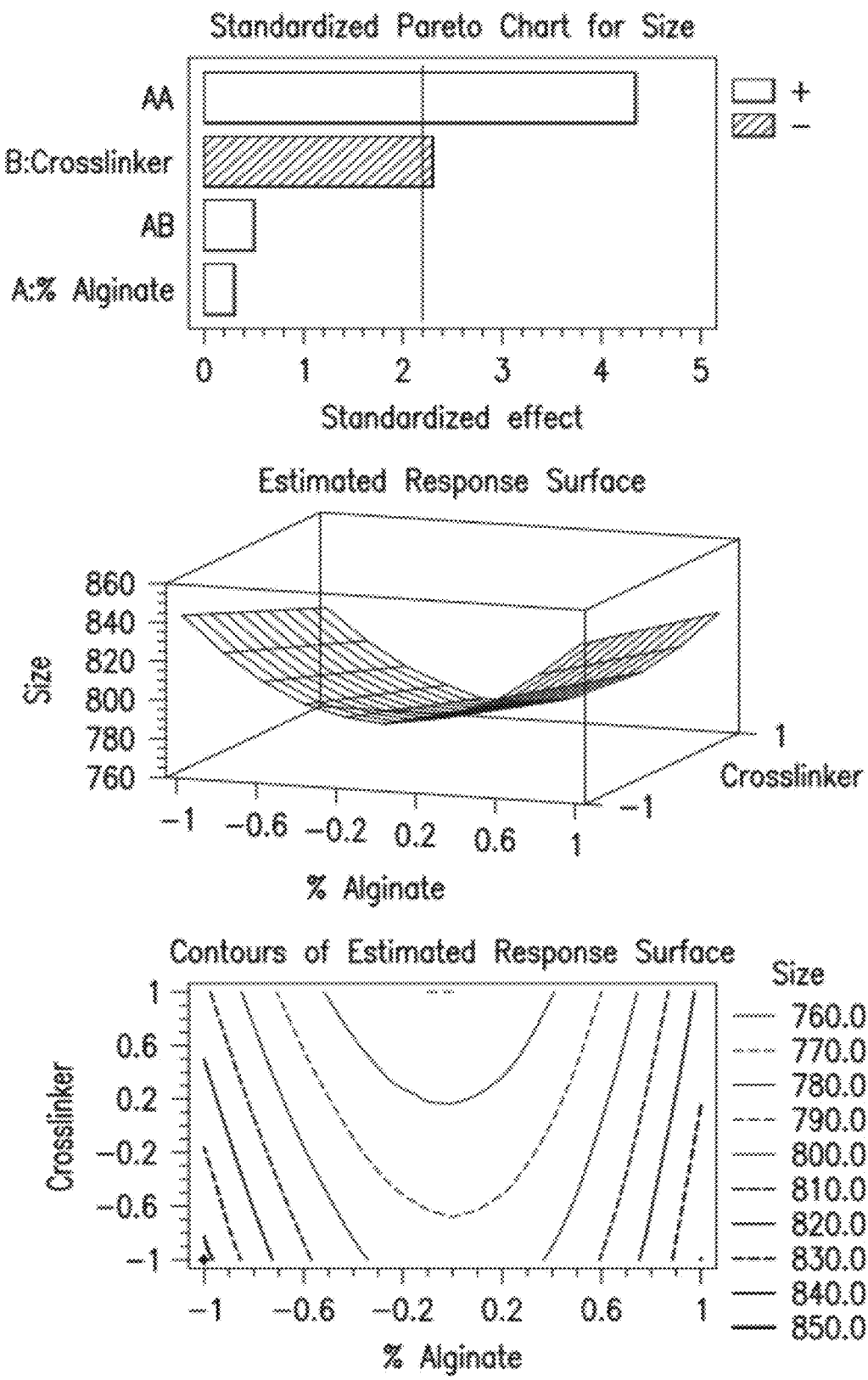
FIG. 10 contains statistical analysis of the effect of the formulation's parameters on both particle size and equilibrium swelling of the disclosed magnetic hydrogel nanoparticles.
Figures 2, 10:
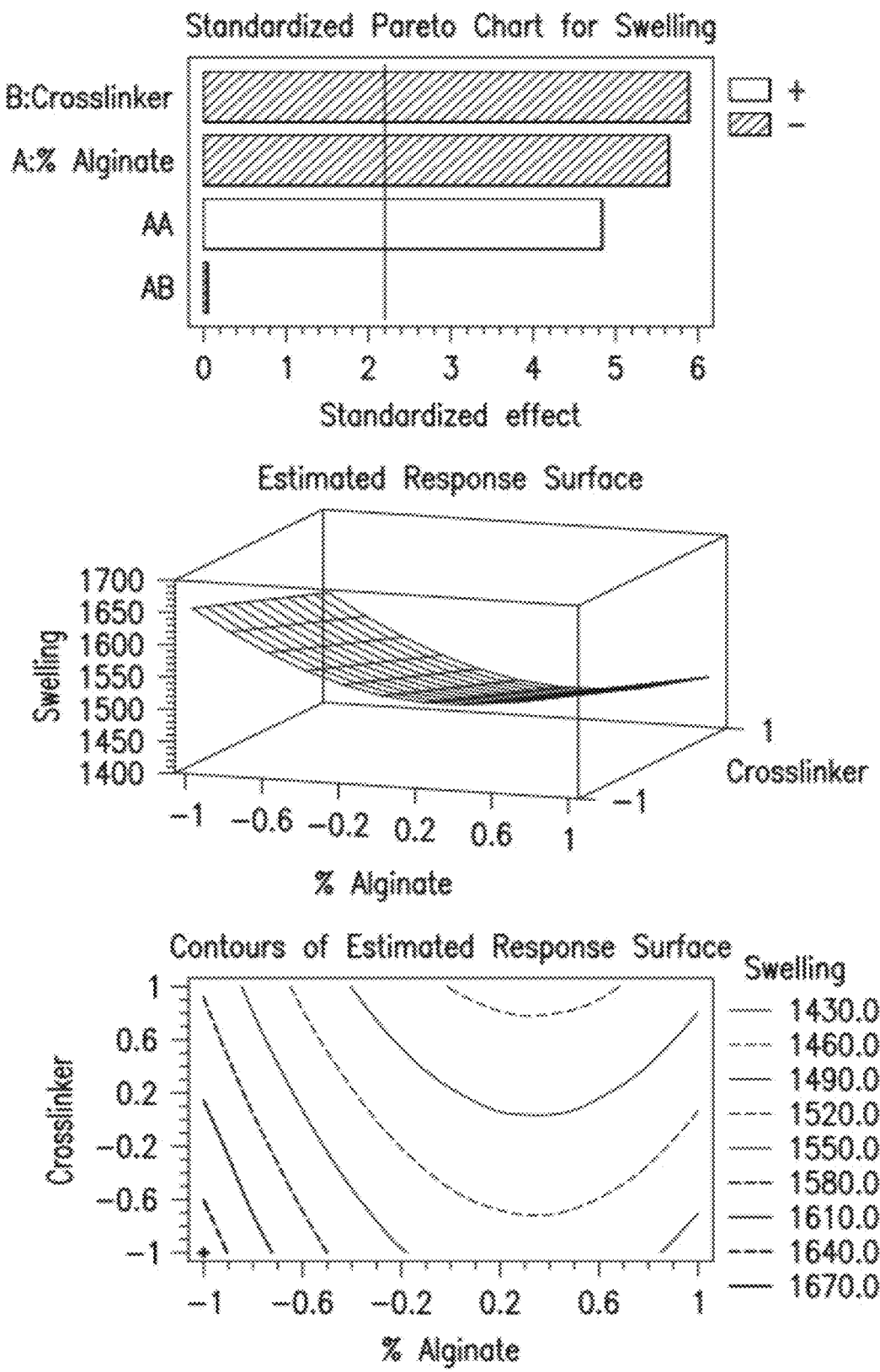

In case of particle size, as apparent from the standardized Pareto chart (FIG. 10-1, top), the type of crosslinking agent can be considered the main factor that controls the size of the disclosed magnetic hydrogel nanoparticles. But as mentioned previously, these differences in particle size do not appear to be practically significant. The surface response methodology was also applied to investigate the way in which the particle size would respond to the parameters variations (FIG. 10-1, middle). The diagram reveals that the smallest particle sizes were obtained when the alginate % was maintained in its lower value (−1 corresponding to 70%) with the use of a crosslinker mixture (coded as +1). These obtained results are consistent with the particle size data determined experimentally and can be used in future studies to design experimental parameters that may result in a wider range of particle sizes produced. These parameters include the following: different atomizer output particle size, drying/conditioning of aerosol prior to crosslinking, concentrations of the hydrogel components, reaction temperatures, among other factors.

In the case of the equilibrium swelling, as shown in the standardized Pareto chart (FIG. 10-2, top), the type of crosslinking agent can be considered the major factor that controls the equilibrium swelling of the hydrogel nanoparticles, followed by the alginate %. Hence, variation of any of these two parameters would likely have a more relevant influence on the swelling values attained at equilibrium. As apparent in the surface response diagram (FIG. 10-2, middle), the lowest swelling values were attained when the alginate % was maintained in its higher value (+1 corresponding to 100%) with the use of a $Ca^2$/copolymer mixture as a crosslinking agent (coded as +1). These results are in agreement with the equilibrium swelling data as determined experimentally.

Example 8

Preparation of Hydrogel Nanoparticles

Hydrogel nanoparticles were developed via the air-jet nebulization of small sprayed droplets of alginate solutions followed by either ionotropic gelation in aqueous $Ca^{2+}$ solution or both ionotropic and polyelectrolyte complexation in (1:1) aqueous solution of PEG-g-Cs/$CaCl_2$ as crosslinkers. Briefly, a (0.1% w/v) aqueous solution of the synthesized copolymer, PEG-g-Cs was prepared using a few mLs of 0.06 M acetic acid and then made up to the predetermined volume with distilled water. Also, aqueous solutions of $CaCl_2$ (0.2 M) and sodium alginate (0.5 and 1% w/v) were prepared. Alginate solutions of different concentrations were added to different air-jet nebulizers (Pari LC Plus and Aerotech II) and aerosolized by using compressed air delivered at controlled pressures of 20 and 40 psi (Table 2). The generated sprayed droplets, where then collected into the crosslinking solutions containing either $CaCl_2$ (0.2 M) or a (1:1) mixture of PEG-g-Cs/$CaCl_2$ under continuous mild stirring throughout a vacuum system leading to gelation of the aerosol droplets. The obtained swollen hydrogel nanoparticles were transferred to scintillation vials and freeze-dried. The obtained hydrogel powders were then washed with water to remove any residual crosslinker and then refreeze-dried. The yield (%) of the resulting dry hydrogel nanoparticles powders was calculated and then the powders were stored at room temperature in a desiccator until further investigation

TABLE 2

The investigated parameters and the compositions of the hydrogel nanoparticles developed by the disclosed spray gelation-based method.

| Nebulizer | Sample code | Air pressure (psi) | Crosslinker | % Alginate (w/v) |
|---|---|---|---|---|
| Pari LC Plus | PN1 | 20 | $CaCl_2$ | 0.5 |
| | PN2 | 20 | PEG-g-Cs/$CaCl_2$ | 0.5 |
| | PN3 | 40 | $CaCl_2$ | 0.5 |
| | PN4 | 40 | PEG-g-Cs/$CaCl_2$ | 0.5 |
| | PN5 | 20 | $CaCl_2$ | 1 |
| | PN6 | 20 | PEG-g-Cs/$CaCl_2$ | 1 |
| | PN7 | 40 | $CaCl_2$ | 1 |
| | PN8 | 40 | PEG-g-Cs/$CaCl_2$ | 1 |
| Aerotech II | AN1 | 20 | $CaCl_2$ | 0.5 |
| | AN2 | 20 | PEG-g-Cs/$CaCl_2$ | 0.5 |
| | AN3 | 40 | $CaCl_2$ | 0.5 |
| | AN4 | 40 | PEG-g-Cs/$CaCl_2$ | 0.5 |
| | AN5 | 20 | $CaCl_2$ | 1 |
| | AN6 | 20 | PEG-g-Cs/$CaCl_2$ | 1 |
| | AN7 | 40 | $CaCl_2$ | 1 |
| | AN8 | 40 | PEG-g-Cs/$CaCl_2$ | 1 |

As shown in Table 2, several hydrogel nanoparticle formulations were obtained based on the combination of parameter such as nebulizers, crosslinkers and applied air pressure. Nebulizers have been therapeutically used to convert liquids into aerosols and it has been proven that they can produce fine droplets (~1 µm) (Bailey et al., *Med Res Rev* 29:196-212, 2009). Alginate solutions of different concentrations were added to the nebulizer, the driving force for the atomization of the alginate droplets is generated by the high-velocity air that passes through a small nozzle within the device and at the same time draws fluid to be nebulized via the venturi effect (Hess, *Respiratory Care* 45:609-622, 2000). Then, after the sprayed anionic polyelectrolyte alginate solutions were passed directly into an aqueous solution containing divalent cations such as $Ca^{2+}$ or polycation such as PEG-g-Cs copolymer. Following this rapid reaction, insoluble network structures were formed and gelation was induced because of the diffusion of cations into the alginate droplets or by the formation of polyelectrolyte complexes, forming three dimensional lattice of ionically crosslinked polymer and resulting in the formation of hydrogel nanoparticles, which were later dried by freeze-drying. After the final powder was collected and weighed, the spray gelation yield was calculated resulting in a range between 30-90%.

Aerotech II and Pari LC Plus nebulizers were chosen in this study because of the several literature reports (McPeck et al., *Chest* 111:1200-1205, 1997; Barry et al., *European Respiratory J* 13:1164-1169, 1999; Bauer et al., *Respiratory Care* 54:1342-1347, 2009). Aerotech II and Pari LC Plus were found to have greater aerosol output efficiencies, produce droplets with small sizes (<5 µm), and show higher efficiency in the aerosolization of viscous formulations. Also, it has been reported (Hess, *Respiratory Care* 45:609-622, 2000) that the main determinants of a droplet size produced by a nebulizer include the characteristics of the solutions such as viscosity, and the velocity of the gas. Thus the influence of polymer concentration, air pressure, and crosslinker type on droplet sizes was studied in these investigations.

Figures 13A, 13B:
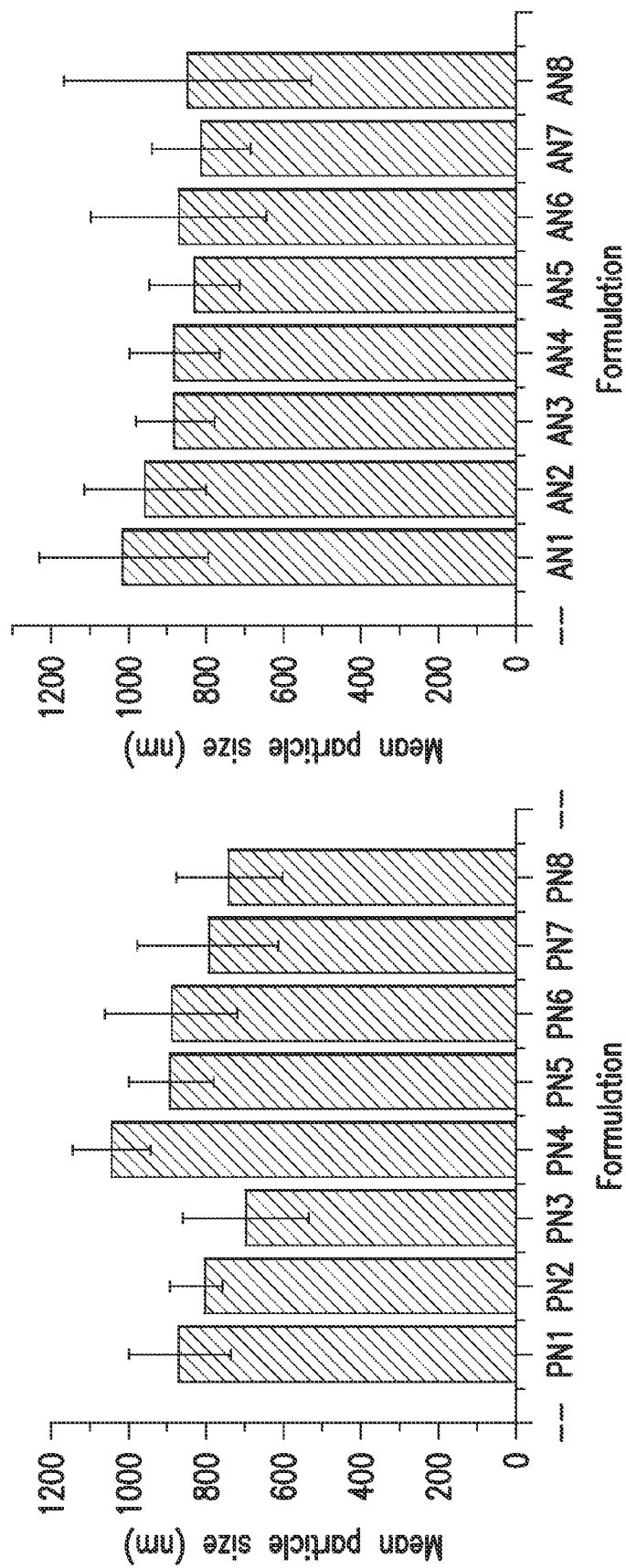
FIG. 13 is a pair of graphs showing the mean particle size (diameter, d, m) of the dried hydrogel nanoparticles produced by spray gelation-based method using the a) Pari LC Plus and b) Aerotech II nebulizers.

Particle size was measured as discussed above. FIG. 13 shows the influence of the formulation's parameters on the mean particle size of the hydrogel nanoparticles. The mean size of the hydrogel nanoparticles developed using the Pari LC Plus and Aerotech II nebulizers was found to be 842 and 886 nm, respectively with a standard deviation of 7-12%. To verify the existence of significant differences between both sets of particle size data upon using different nebulizers (Pari LC Plus or Aerotech II), statistical analysis was carried out. The obtained result showed minor statistical differences (p=0.0445) (Table 3), so these statistical differences were attribute to practical differences. Moreover, as shown in FIG. 13a Pari LC Plus generated hydrogel nanoparticles with smaller sizes using 1% alginate solutions than when 0.5% alginate solutions were used. This decrease in the size of the nanoparticles can be attributed to the higher extent of crosslinking occurred upon using higher (1%) concentration of sodium alginate. The data also showed that the air pressure is a determinant factor on the droplet size. Increasing the velocity of the air in the nebulizer upon applying higher pressures (40 psi) has induced the formation of smaller particles. The influence of the type of crosslinker on the particle size was not clearly seen.

In contrast, Aerotech II formulations showed relatively larger particle sizes (FIG. 13b). Nevertheless, they presented the narrowest particle size distribution. This effect can be related to the presence of a baffle that covers the aerosol stream region preventing the formation of larger particles due to the centered pressure applied during atomization into a constant direction. As observed in Pari LC Plus, smaller hydrogels particles were formed when a pressure of 40 psi was applied to the Aerotech II nebulizer (AN5-AN8) as a consequence of the high air velocity entrained into the nebulizer. In this case, it was found that increasing the concentration of the alginate solutions to 1% (AN5-AN8) led to a decrease in the particle size which probably due to the extensive crosslinking. In addition, it appears that the type of the crosslinkers, used in this study, has no significant effect onto the size of the disclosed particles (see Table 3).

TABLE 3

Summary of the analysis of variance for mean particle size

| Factor | Sum of Squares | DF | Mean Square | F-Ratio | *p-Value |
|---|---|---|---|---|---|
| Nebulizer | 23232.0 | 1 | 23232.0 | 4.34 | 0.0445 |
| Crosslinker | 11907.0 | 1 | 11907.0 | 2.23 | 0.1446 |
| Alginate | 42126.8 | 1 | 42126.8 | 7.88 | 0.0081 |
| Air Pressure | 34347.0 | 1 | 34347.0 | 6.42 | 0.0159 |

*p < 0.05,
DF = Degree of Freedom

Example 9

Swelling Study

Figure 14:
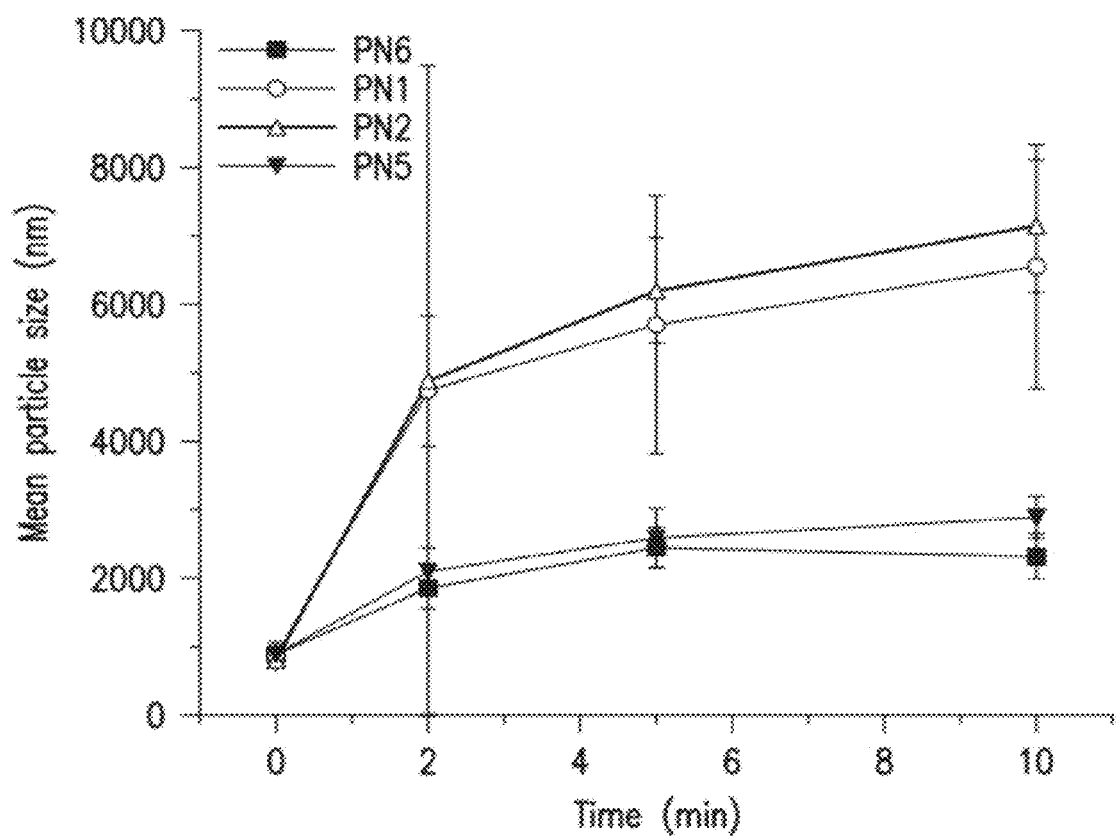
FIG. 14 is a graph showing swelling behavior of hydrogel nanoparticles based on the concentration of alginate solutions (PN1 y PN2, 0.5% and PN5 y PN6, 1%).

A swelling equilibrium curve of the hydrogel nanoparticles in water from Example 8 is shown in FIG. 14. The effect of alginate concentrations and type of crosslinker on the swelling behavior of the formulations developed using Pari LC Plus, (PN1, PN2, PN5, and PN6) was investigated. The swelling patterns were estimated according to the increase in the mean diameter (nm) of hydrogel nanoparticles after 2, 5 and 10 min by microscopy. As seen in FIG. 14, the formulations containing a concentration of 0.5% alginate (PN1 and PN2), showed a faster initial swelling after 2 min in comparison with the formulations of 1% alginate, increasing their size more than four times. For example, the size of PN1 and PN2 increased from 869 and 807 nm when dry to 4,647 and 4,884 nm after 2 min, respectively. A continued increase in the mean diameter was observed after 10 min, where the hydrogel particles reached values of 6,551 and 7,144 nm, respectively. Also, it can be noted that by increasing the alginate concentration to 1%, reduced hydrogel swelling values were observed. These data are consistent with the crosslinking extent, where, as the alginate concentration increases the interaction of alginate with the polyvalent cations is enhanced, leading to the formation of a smaller mesh size in the meshwork that limits the access of water. In this way, PN5 and PN6 formulations showed smaller sizes when swollen. In the effect of the type of crosslinker in the swelling curves, it was observed that when a 0.5% alginate was used, both $CaCl_2$ and the PEG-g-Cs/$CaCl_2$ mixture showed a similar behavior on the swelling size of the hydrogel nanoparticles. The results also showed that by using either $CaCl_2$ or PEG-g-Cs/$CaCl_2$ the achieved crosslinking's degrees were very similar. The same phenomenon was observed in the 1% alginate formulations. These data were confirmed by the p-value obtained by the analysis of variance, which showed a nonsignificant difference between both crosslinkers (Table 3).

Example 10

Scanning Electronic Microscopy

Figure 15:
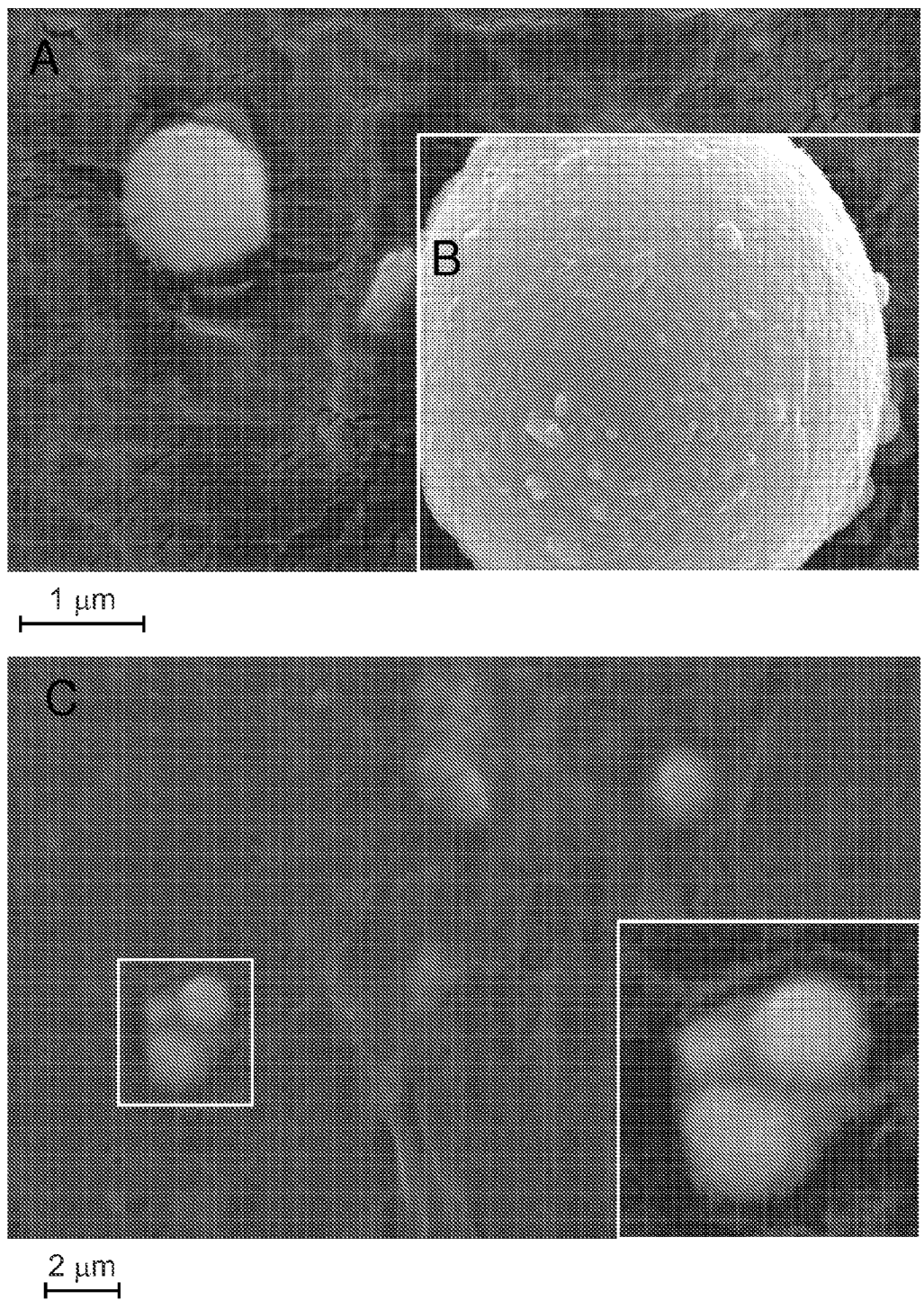
FIG. 15 is a group of scanning electron micrographs of alginate nanoparticles produced using the Aerotech II nebulizer using spray gelation: a, b) AN7 and c) AN8.

FIG. 15 shows the scanning electron micrographs of the morphology of the hydrogel nanoparticles generated by the spray gelation in Example 8. The disclosed hydrogel nanoparticles presented, in general, spherical shapes with highly rough surfaces, especially in Pari LC Plus formulations, where 1% alginate solutions and 40 psi air pressure were applied (FIG. 15b). Furthermore, Aerotech II formulations also presented spherical shapes under the same conditions (FIG. 15c).

Example 11

Analysis of the Hydrogel Nanoparticles Synthesis by a $2^k$ Factorial Design

In this study, a discontinuous 2k factorial design was carried out to determine the effects of nebulizer, crosslinker, air pressure, and alginate concentration and their interaction on the obtained hydrogel formulations. Considering that the combination of those factors would modify the properties of the nanoparticles, variations of each factor in two levels were analyzed. The two levels of each factor were coded with a low and high level to be analyzed by response surface methodology and Pareto charts. In this design, the particle size and equilibrium swelling values were used as response variables. Since type of nebulizer and crosslinker are not numeric values, −1 and 1 levels were assigned for each nebulizer and crosslinker (Table 4).

TABLE 4

Summary of the factors and response variables used in the experimental 2k design.

| Factor | Low value | High value | Units |
|---|---|---|---|
| Alginate concentration | 0.5 | 1.0 | % (w/v) |
| Air pressure | 20 | 40 | psi |
| Nebulizer | Pari LC Plus | Aerotech II | — |
| Crosslinker | $CaCl_2$ | PEG-g-Cs/$CaCl_2$ | — |

Figure 16:
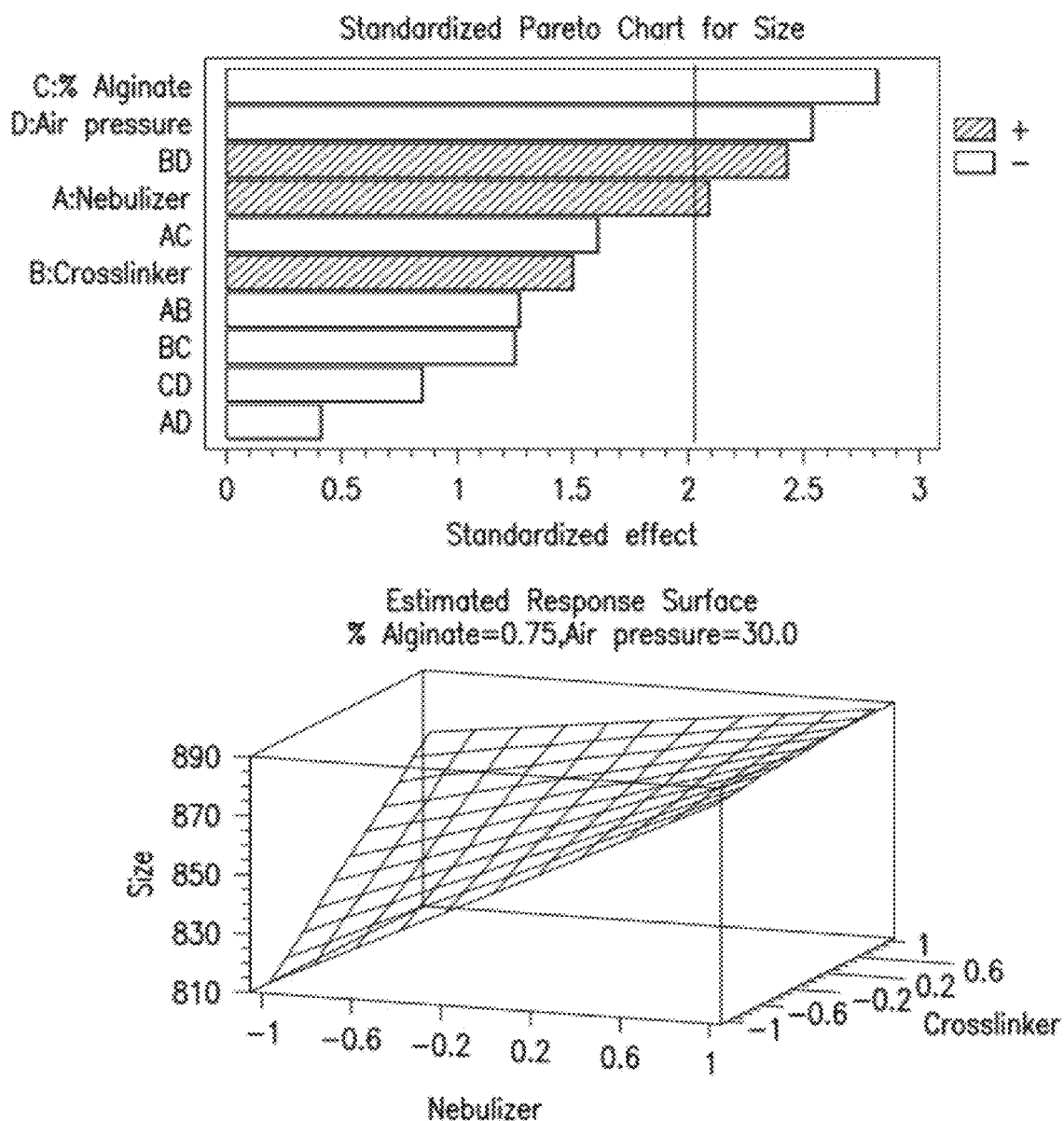
FIG. 16 contains statistical estimations of the effect of a formulation's parameters on the particle size of the hydrogel nanoparticles represented by a) Pareto chart, and b) response surface methodology.

The analysis of variance for particle size obtained by Statgraphics 5.0 shows the most influential factors in the size and swelling behavior of the hydrogel nanoparticles at the 95% confidence level. Then, all those factors and/or interactions with a $p<0.05$ value will be consider the most relevant factor for either particle size or swelling. Thus, the obtained results showed that four effects are influencing the particle size. Those effects and their interactions can be clearly seen in the standardized Pareto chart (FIG. 16, top), where it is showed that alginate concentration, air pressure, the interaction between crosslinker and air pressure, and the type of nebulizer are the main factors that modify the size of the hydrogel nanoparticles. The order in which they appear corresponds to their importance in affecting the particle size. From the figure, it seems that the alginate concentration is the principal determinant of the size of nanoparticles, followed by the air pressure. Therefore, modification of any of these two factors would have a more relevant effect on the particle size than the other factors. Surface response methodology was also used to illustrate the way in which particle size would respond to variations in the parameter used during the production of nanoparticles (FIG. 16, bottom). The results showed that, when the alginate concentration and air pressure are maintained in their intermediate values, by using Pari LC Plus nebulizer, smaller particle sizes can be obtained. The effect of the type of crosslinker is considered not significantly different (see Table 4). This effect can be clearly observed by the pronounced slope that gives rises to the minimum peak on the presented surface. Therefore, the data shown here are consistent with the particle size data found experimentally, where Pari LC produced smaller particle sizes than Aerotech II.

Figure 17:
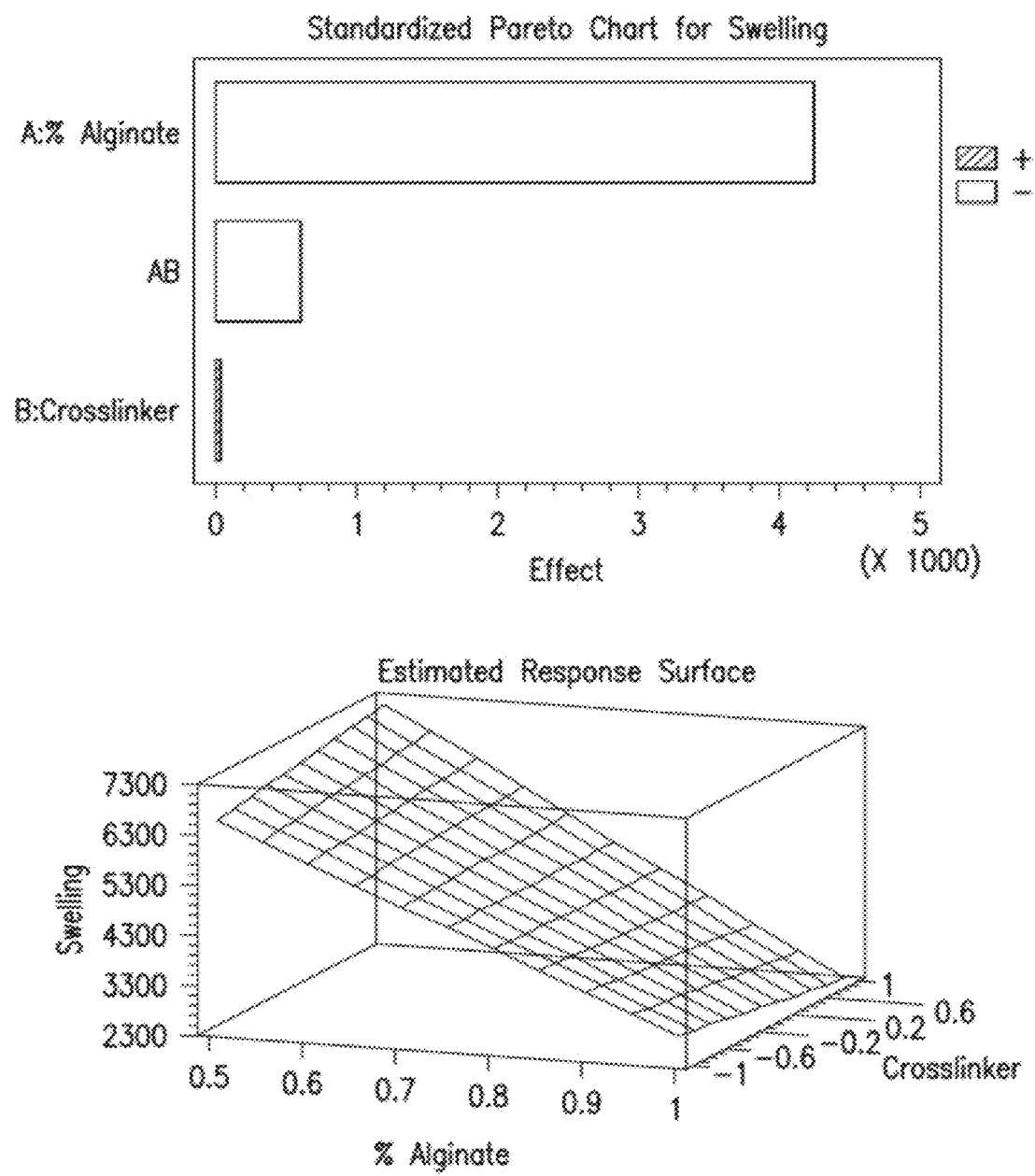
FIG. 17 contains (a) a Pareto chart, and b) response surface methodology graph of the effect of alginate concentration and crosslinker on the swelling behavior of hydrogel nanoparticles.
Figure 18:
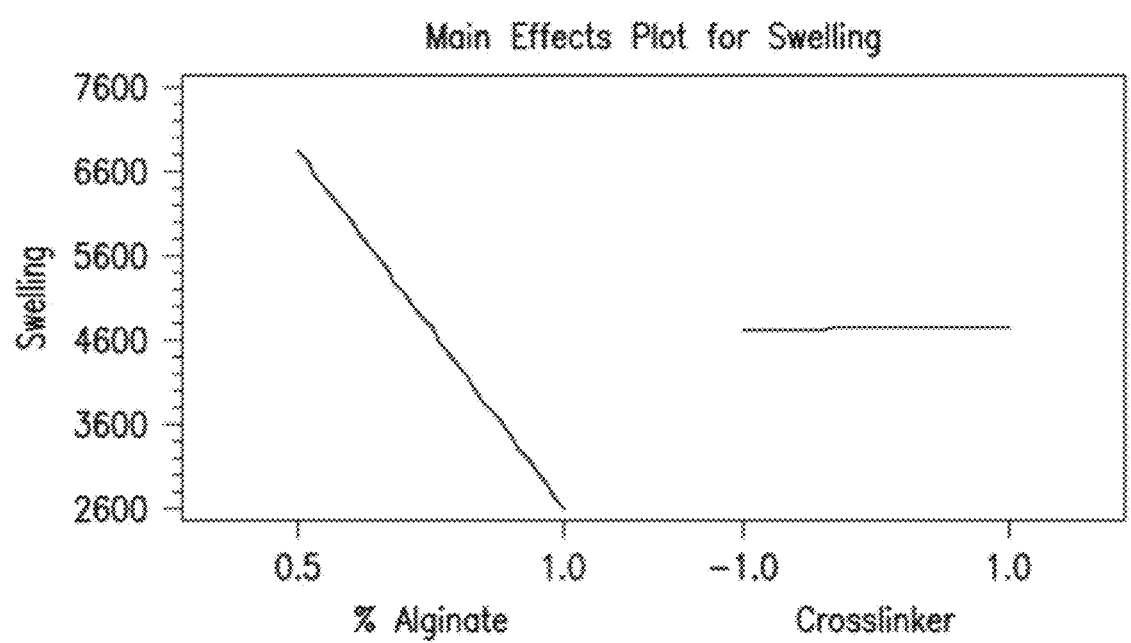
FIG. 18 is a graph showing the effect of alginate concentration and type of crosslinker on the swelling size of the hydrogel nanoparticles. It is shown that the type of crosslinker does not have a significant effect on the swelling of nanoparticles.

In the case of the swelling behavior, the crosslinker and alginate concentration were the factors modified in this study for Pari LC Plus formulations and the results in Pareto chart (FIG. 17, top), showed that alginate concentration is a fundamental factor in the processing of the nanoparticles and any modification in its value would lead to an increase or reduction in the swelling values. According with the surface response methodology graph, nanoparticles with 0.5% alginate would reach a larger size when swollen than the formulations with 1% alginate (FIG. 17, bottom). These data are very consistent with results seen in FIG. 14. Also, the interaction between both factors plays an important function, showing dependence on the alginate concentration used. However, the type of the crosslinker by itself does not have an effect on the swelling behavior of nanoparticles (FIG. 18).

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of producing a polymeric particle, comprising:
   a. providing an aqueous or non aqueous mixture of a polymer;
   b. aerosolizing the mixture; and
   c. contacting the aerosol with a crosslinking solution, wherein the crosslinking solution comprises a second polymer, thereby producing the particle.

2. The method of claim 1, further comprising adding an oligouronate mixture to the polymer mixture.

3. The method of claim 1, wherein the crosslinking solution comprises a divalent cation.

4. The method of claim 3, wherein the divalent cation is $Ca^{2+}$, $Ba^{2+}$, or $Sr^{2+}$.

5. The method of claim 1, wherein the polymer is alginate and/or an alginate salt.

6. The method of claim 1, wherein the second polymer is chitosan or a chitosan derivative.

7. The method of claim 6, wherein the chitosan is derivatized with polyethylene glycol, stearic acid, or cholanic acid.

8. The method of claim 1, wherein the crosslinking solution is an aqueous solution comprising chitosan derivatized with polyethylene glycol and $Ca^{2+}$.

9. The method of claim 8, wherein the chitosan and $Ca^{2+}$ are in a 1:1 ratio.

10. The method of claim 1, further comprising adding a magnetic or magnetizable agent to the aqueous mixture of alginate.

11. The method of claim 10, wherein the agent is magnetite, maghemite, or superparamagnetic iron oxide nanoparticles.

12. The method of claim 1, further comprising adding a bioactive agent to the aqueous mixture of polymer.

13. The method of claim 1, wherein aerosolizing step involves spraying the polymer mixture through an air jet nebulizer.

14. The method of claim 1, further comprising collecting and drying the polymer particles.

15. The method of claim 14, wherein the particles are dried by spray drying or freeze drying.

16. The method of claim 1, wherein the mean particle size is from about 100 nm to about 10 μm.

17. The method of claim 1, wherein the polymer is from about 70 to about 80% by weight of the particle.

18. The method of claim 1, wherein the polymer is from about 80 to about 90% by weight of the particle.

19. The method of claim 1, wherein the polymer is greater than 90% by weight of the particle.

20. The method of claim 1, further comprising repeating steps a through c with the particle.

* * * * *